(12) United States Patent
Perera et al.

(10) Patent No.: US 12,343,473 B2
(45) Date of Patent: Jul. 1, 2025

(54) METHOD AND APPARATUS FOR TREATING HYPERAROUSAL DISORDER

(71) Applicant: ResMed Pty Ltd, Bella Vista (AU)

(72) Inventors: Bodiyabaduge Dimithri Joseph Perera, Sydney (AU); Dinesh Ramanan, Telopea (AU); Gordon Joseph Malouf, Sydney (AU); Liam Holley, Sydney (AU); Neha Banodkar, Sydney (AU)

(73) Assignee: ResMed Pty Ltd (AU)

( * ) Notice: Subject to any disclaimer, the term of this patent is extended or adjusted under 35 U.S.C. 154(b) by 1243 days.

(21) Appl. No.: 15/733,438

(22) PCT Filed: Feb. 15, 2019

(86) PCT No.: PCT/AU2019/050123
§ 371 (c)(1),
(2) Date: Jul. 30, 2020

(87) PCT Pub. No.: WO2019/157563
PCT Pub. Date: Aug. 22, 2019

(65) Prior Publication Data
US 2021/0330910 A1    Oct. 28, 2021

(30) Foreign Application Priority Data
Feb. 15, 2018 (AU) ............................... 2018900477

(51) Int. Cl.
*A61M 16/00* (2006.01)
*A61B 5/00* (2006.01)

(52) U.S. Cl.
CPC ........... *A61M 16/0069* (2014.02); *A61B 5/00* (2013.01); *A61M 16/0003* (2014.02);
(Continued)

(58) Field of Classification Search
CPC ..... A61B 5/0816; A61B 5/01; A61B 5/02416; A61B 5/0531; A61B 5/11;
(Continued)

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| DE | 1168608 B | 4/1964 |
| WO | 2013020167 A1 | 2/2013 |

(Continued)

OTHER PUBLICATIONS

PCT Notification of Transmittal of International Search Report and the Written Opinion of the International Searching Authority, or the Declaration issued in PCT/US2019/050123 on May 13, 2019.
(Continued)

*Primary Examiner* — Justine R Yu
*Assistant Examiner* — Alexander Morales
(74) *Attorney, Agent, or Firm* — Botos Churchill IP Law LLP

(57) ABSTRACT

Systems or apparatus may be configured with method(s) for hyperarousal disorder such as for determining settings that control respiratory therapy for slowing a patients breathing. They may be configured to determine an interim target breathing rate less than a current spontaneous rate. They may be configured to derive target inspiratory time and expiratory times based on the interim target breathing rate. They may be configured to compute, with first function(s), a parameter set for generating a variable treatment pressure waveform based on target inspiratory/expiratory times. They may be configured to determine pressure settings by generating the waveform with the computed parameter set and
(Continued)

second function(s). They may be configured to reduce the interim target breathing rate in response to a subsequent spontaneous breathing rate slowing down toward the interim target rate. They may be configured to generate feedback such as graphics/sound to provide information to promote slowing of breathing.

26 Claims, 14 Drawing Sheets

(52) U.S. Cl.
CPC ... *A61M 16/026* (2017.08); *A61M 2016/0027* (2013.01); *A61M 2016/0036* (2013.01); *A61M 2205/3331* (2013.01); *A61M 2205/505* (2013.01); *A61M 2205/584* (2013.01); *A61M 2230/42* (2013.01)

(58) Field of Classification Search
CPC .......... A61M 16/0069; A61M 16/0003; A61M 16/026; A61M 2016/0027; A61M 2016/0036; A61M 21/02; A61M 16/06; A61M 16/1005; A61M 16/1055; A61M 16/208; A61M 2016/0018; A61M 2021/0016; A61M 2021/0022; A61M 2021/0027; A61M 2021/0044; A61M 16/024; A61M 16/00; A61M 16/107; A61M 2016/0033; A61M 2205/3331; A61M 2205/505; A61M 2205/584; A61M 2230/42; A61M 2205/15; A61M 2205/18; A61M 2205/21; A61M 2205/3303; A61M 2205/3365; A61M 2205/3584; A61M 2205/3592; A61M 2205/42; A61M 2230/40; A61M 2205/3368; A61M 2230/06; A61M 2230/50; A61M 2230/63; A61M 2205/581; A61M 2205/582; A61M 2205/583

USPC .................................................. 128/204.23
See application file for complete search history.

(56) References Cited

U.S. PATENT DOCUMENTS

| | | | |
|---|---|---|---|
| 7,556,038 | B2 | 7/2009 | Kirby et al. |
| 7,866,944 | B2 | 1/2011 | Barton et al. |
| 8,523,758 | B1 | 9/2013 | Kirby et al. |
| 8,636,479 | B2 | 1/2014 | Barton et al. |
| 8,638,014 | B2 | 1/2014 | David |
| 9,717,868 | B2 | 8/2017 | Truschel et al. |
| 9,974,923 | B2 | 5/2018 | Laura Lapoint et al. |
| 11,534,563 | B2* | 12/2022 | Martin .............. A61M 16/0003 |
| 2006/0162727 | A1* | 7/2006 | Biondi .............. A61M 16/0051 128/204.22 |
| 2008/0035147 | A1* | 2/2008 | Kirby .................. A61M 16/026 128/204.23 |
| 2010/0108066 | A1 | 5/2010 | Martin et al. |
| 2014/0007877 | A1 | 1/2014 | O'Connor |
| 2014/0326241 | A1* | 11/2014 | Martin ................ A61M 16/026 128/204.23 |
| 2017/0028146 | A1* | 2/2017 | Nandigama ....... A61M 16/0434 |
| 2017/0326314 | A1 | 11/2017 | Chewe et al. |
| 2018/0192920 | A1* | 7/2018 | Rosenblood ........... A61B 5/486 |

FOREIGN PATENT DOCUMENTS

| | | |
|---|---|---|
| WO | 2016065411 | 5/2016 |
| WO | 2018018074 A1 | 2/2018 |

OTHER PUBLICATIONS

West, John B., "Respiratory Physiology", Lippincott Williams & Wilkins, 9th Edition published 2012.

* cited by examiner

METHOD AND APPARATUS FOR TREATING HYPERAROUSAL DISORDER

1. CROSS-REFERENCE TO RELATED APPLICATIONS

The present application is a national phase entry under 35 U.S.C. § 371 of International Application No. PCT/AU2019/050123 filed Feb. 15, 2019, published in English, which claims priority from Australian Provisional Patent Application No. 2018900477 filed Feb. 15, 2018, all of which are incorporated herein by reference.

2. BACKGROUND OF THE TECHNOLOGY

2.1 Field of the Technology

The present technology relates to one or more of the detection, diagnosis, treatment, prevention and amelioration of respiratory-related disorders. In particular, the present technology relates to medical devices or apparatus, and their use such as for hyperarousal disorder.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones). CSR is a form of periodic breathing.

Respiratory failure is an umbrella term for respiratory disorders in which the lungs are unable to inspire sufficient oxygen or expire sufficient $CO_2$ to meet the patient's needs. A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising.

2.2.1.1 Insomnia

Insomnia is defined as problems falling asleep and staying asleep, or as non-restorative sleep, that persist(s) longer than one month and result(s) in functional impairment. Two kinds of insomnia are defined: (i) sleep onset insomnia, i.e. difficulty falling asleep; (ii) sleep maintenance insomnia, i.e. frequent awakenings during the night or early morning awakenings. Insomnia can be acute, intermittent, or chronic (duration greater than six months). Chronic insomnia is a common complaint in the general population (prevalence may be between 6% and 18%) as well as in various subpopulations such as the elderly, psychiatric patients, and shift workers. A current theory of insomnia is that due to any number of reasons, insomniacs are in a state of physiologic hyperarousal over the 24-hour period, and that this hyperarousal leads to sleep disturbances. Insomnia can occur as a symptom of another disorder, as a disorder in its own right, or both. Insomnia that begins as a symptom of another disorder (comorbid insomnia) can develop into a disorder in its own right.

Insomnia is frequently associated with psychological disorders. In Krakow's 2010 study, 87% of insomnia patients reported a history of at least one of the following: depression, anxiety disorder, post-traumatic stress disorder (PTSD), panic disorder, schizophrenia, bipolar disorder, obsessive-compulsive disorder (OCD), traumatic exposure, or claustrophobia.

Many—but not all—studies have shown higher than expected rates of comorbid SDB with hyperarousal disorders, in particular chronic insomnia, even though the subjects may not report excessive sleepiness.

2.2.2 Therapies

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist patient's breathing and/or maintain adequate oxygen levels in the body by doing some or all of the work of breathing. The ventilatory support is provided via a non-invasive patient interface. NIV has been used to treat OSA, respiratory failure, and periodic breathing. In some forms, the comfort and effectiveness of these therapies may be improved.

Not all respiratory therapies aim to deliver a prescribed therapy pressure. Some respiratory therapies aim to deliver a prescribed respiratory volume, possibly by targeting a flow rate profile over a targeted duration. In other cases, the interface to the patient's airways is 'open' (unsealed) and the respiratory therapy may only supplement the patient's own spontaneous breathing. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, and other respiratory disorders. One mechanism of action is that the high flow rate of air at the airway entrance improves ventilation efficiency by flushing, or washing out, expired $CO_2$ from the patient's anatomical deadspace. HFT is thus sometimes referred to as a deadspace therapy (DST). In other flow therapies, the treatment flow rate may follow a profile that varies over the respiratory cycle.

Evidence for cognitive-behavioural therapy (CBT) as the ideal first-line treatment for insomnia is substantial, but the lack of behavioural sleep medicine specialists both at sleep medical centres and in the medical community at large has limited its application. In contrast, pharmacotherapy for insomnia is well established. Traditional standards indicate prescribed medication for acute, transient, or situational insomnia, and the prescribing instructions may recommend nightly use for a few weeks or a few times per week for longer intervals.

However, a sizable proportion of insomniacs may not experience adequate symptomatic relief despite continuing to use nightly prescription medications.

A need therefore exists for improved methods and apparatus for treatment of hyperarousal disorders including insomnia.

2.2.3 Treatment Systems

A hyperarousal disorder treatment system may comprise a Respiratory Pressure Therapy Device (RPT device), an air circuit, a humidifier, and a patient interface.

2.2.3.1 Patient Interface

A patient interface may be used to interface respiratory equipment to its user, for example by providing a flow of air to an entrance to the airways. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 $cmH_2O$. For other forms of therapy, such as the delivery of oxygen, the patient interface may not include a seal sufficient to facilitate delivery to the airways of a supply of gas at a positive pressure of about 10 $cmH_2O$.

2.2.3.2 Respiratory Pressure Therapy (RPT) Device

One known RPT device used for treating sleep disordered breathing is the S9 Sleep Therapy System, manufactured by ResMed. Another example of an RPT device is a non-invasive ventilator.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

2.2.3.4 Air Circuit

An air circuit is a conduit or a tube constructed and arranged in use to allow a flow of air to travel between two components of the treatment system, such as the RPT device and the patient interface.

3. BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

The present technology generally relates to apparatus and methods used in the diagnosis, amelioration, treatment or prevention of hyperarousal disorders.

In what follows, the term "insomnia" is used to stand in for all hyperarousal disorders including insomnia, anxiety, and PTSD, except where indicated otherwise.

One aspect of the present technology comprises methods and apparatus for treating insomnia by means of paced breathing. The paced breathing may be combined with biofeedback. Such treatment methods and apparatus may be useful as a calming intervention, either during daytime sessions, before going to sleep, or upon awakening during the night. They may also be useful to aid acclimatisation to mask and therapy device before starting respiratory pressure therapy for conditions such as OSA and respiratory failure.

Some versions of the present technology may include a method of determining settings for control of bi-level respiratory pressure therapy for slowing a patient's breathing. The method may include determining an interim target breathing rate that may be less than a current spontaneous breathing rate of the patient. The method may include deriving a target inspiratory time and a target expiratory time, each of the target inspiratory time and the target expiratory time being derived based on the interim target breathing rate. The method may include computing, with one or more first functions, a set of parameters for generating a variable treatment pressure waveform based on the target inspiratory time and the target expiratory time. The method may include determining pressure settings by generating the variable treatment pressure waveform with the computed set of parameters and one or more second functions. The method may include reducing the interim target breathing rate in response to a subsequent spontaneous breathing rate of the patient slowing down toward the interim target breathing rate.

In some versions, the one or more second functions when applied with the computed set of parameters may generate the variable treatment pressure waveform with an inspiratory portion having a continuous rise until the target inspiratory time is reached. The one or more second functions when applied with the computed set of parameters may generate the variable treatment pressure waveform with an expiratory portion having a continuous fall until the target expiratory time may be reached. The one or more second functions may be in multiple part form (e.g., two-part form). One part may generate a target inspiratory portion between a trigger point and the target inspiratory time. Another part may generate a target expiratory portion between a cycle point and a target total time. The one or more second functions for the target inspiratory portion may have a parametrised form as follows: $K1+(K2\times t)^{K3}$ wherein t represents time and K1, K2, and K3 are parameters of the one or more second functions for the target inspiratory portion. The one or more second functions for the target expiratory portion may have a parametrised form as follows: $K4-(K5\times(t-tgtTi))^{K6}$ wherein t represents time and K4, K5, and K6 are parameters of the one or more second functions for the target expiratory portion and tgtTi may be the target inspiratory time. The computing the set of parameters may include computing K2 such that the target inspiratory portion starts from K1 and reaches K4 when t may be equal to the target inspiratory time, wherein K1 and K4 may be predetermined pressure levels and K3 may be a predetermined exponent. The computing the set of parameters may include computing K5 such that the target expiratory portion starts from K4 and reaches K1 when t may be equal to the target total time, wherein K1 and K4 may be predetermined pressure levels and K6 may be a predetermined e.

In some versions, deriving the target inspiratory time and the target expiratory time may include determining a target total time as a reciprocal of the interim target breathing rate. The deriving may further include partitioning the target total time into the target inspiratory time and the target expiratory time. The target total time may be partitioned according to a predetermined target proportion. The method may further include recomputing, with the one or more first functions, the set of parameters for generating the variable treatment pressure waveform based on a second target inspiratory time and a second target expiratory time that are both derived with the reduced interim target breathing rate. In some versions, reducing the interim target breathing rate may include reducing the interim target breathing rate according to a predetermined schedule to an optimal breathing rate. The method may further include aborting the predetermined schedule in response to a sudden increase in the patient's breathing rate. The method may further include accessing a second, predetermined schedule to alter a progress of reductions of the interim target breathing rate for a new therapy session. The accessing of the second predetermined schedule may be based on an assessment of progress of the patient's breathing rate reductions in one or more prior therapy sessions.

In some versions, the method may further include generating biofeedback for the patient. The biofeedback may be configured to further encourage the patient's breathing rate to slow down toward the interim target breathing rate. Generating the biofeedback may include displaying, on a graphical display, an annular graphic. One portion of the annular graphic may represent an inspiratory portion, and another portion of the annular graphic may represent an expiratory portion. Generating the biofeedback may include displaying, on the graphical display, a marker graphic moving along the annular graphic at the target breathing rate. The marker graphic may traverse the inspiratory portion of the annular graphic during the target inspiratory time. The method may further include varying a display characteristic of the marker graphic according to a difference between the target breathing rate and a spontaneous breathing rate of the patient. In some versions, the method may further include controlling a blower to generate the bi-level respiratory pressure therapy according to the determined pressure settings.

Some versions of the present technology may include a respiratory pressure therapy device. The respiratory pressure therapy device may include a blower configured to generate a variable pressure at a patient interface according to a variable treatment pressure waveform. The respiratory pressure therapy device may include at least one sensor configured to detect a spontaneous breathing rate of the patient. The respiratory pressure therapy device may include a controller coupled with the blower and the at least one sensor. The controller may be configured to determine an interim breathing rate target that may be less than a current spontaneous breathing rate of the patient. The controller may be configured to derive a target inspiratory time and a target expiratory time, each of the target inspiratory time and the target expiratory time being derived based on the interim breathing rate target. The controller may be configured to compute, with one or more first functions, a set of parameters for generating the variable treatment pressure waveform based on the target inspiratory time and the target expiratory time. The controller may be configured to determine pressure settings for generating the variable pressure to the patient interface by generating the variable treatment pressure waveform with the computed set of parameters and one or more second functions. The controller may be configured to reduce the interim breathing rate target in response to a subsequent spontaneous breathing rate of the patient slowing down toward the interim breathing rate target. The controller may be configured to control the blower according to the pressure settings.

In some versions, the controller may be configured to implement any one or more of the features of the aforementioned method(s) and/or following method(s) described herein. In some versions, the controller may be further configured to generate biofeedback for the patient. The controller may be further configured to generate biofeedback for the patient by controlling a local external computing device in communication with the controller of the respiratory pressure therapy device.

Some versions of the present technology may include a method of providing biofeedback to a patient, the biofeedback relating to bi-level respiratory pressure therapy being delivered to the patient, the respiratory pressure therapy having a target breathing rate. The method may include displaying, on a graphical display, an annular graphic. One portion of the annular graphic may represent a target inspiratory portion of a respiratory cycle of the patient, and another portion of the annular graphic may represent a target expiratory portion of the respiratory cycle of the patient. The method may include displaying, on the graphical display, a marker graphic moving along the annular graphic at the target breathing rate. The marker graphic may traverse the portion of the annular graphic representing the target inspiratory portion during a target inspiratory time. The method may further include varying a display characteristic of the marker graphic according to a timing difference between the target breathing rate and a spontaneous breathing rate of the patient. The marker graphic may change colour according to the timing difference. The method may further include controlling a sound device to emit an acoustic tone having pitch that may be higher during the target inspiratory portion and lower during the target expiratory portion. The method may further include controlling a sound device to generate a voice speaking an instruction to breathe in at a start of the target inspiratory portion and breathe out at a start of the target expiratory portion.

Some versions of the present technology may include a computing device that may include a display and may include a controller. The controller may be configured to execute any one or more of the features of the aforementioned method(s) and/or following method(s) described herein.

Some versions of the present technology may include a computer-readable medium. The computer-readable medium may have encoded thereon computer-readable instructions that when executed by a controller of a device, such as a respiratory device, cause the controller to perform any one or more of the features of the aforementioned method(s) and/or following method(s) described herein.

The methods/systems/devices/apparatus described herein can provide improved functioning in a processor, such as of a processor of a specific purpose computer, respiratory monitor and/or a respiratory pressure therapy device. Moreover, the methods/systems/devices/apparatus can provide improvements in the technological field of automated management, monitoring and/or treatment of respiratory conditions, including, for example, SDB-comorbid insomnia.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4. BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a treatment system including a patient 1000 wearing a patient interface 3000, in the form of a full-face mask, receiving a supply of air at positive pressure from a RPT device 4000. Air from the RPT device 4000 is humidified in a humidifier 5000, and passes along an air circuit 4170 to the patient 1000.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows a patient interface in the form of a nasal mask in accordance with one form of the present technology.

4.4 RPT Device

4.5 Humidifier

Figure 1:
Figure 2:
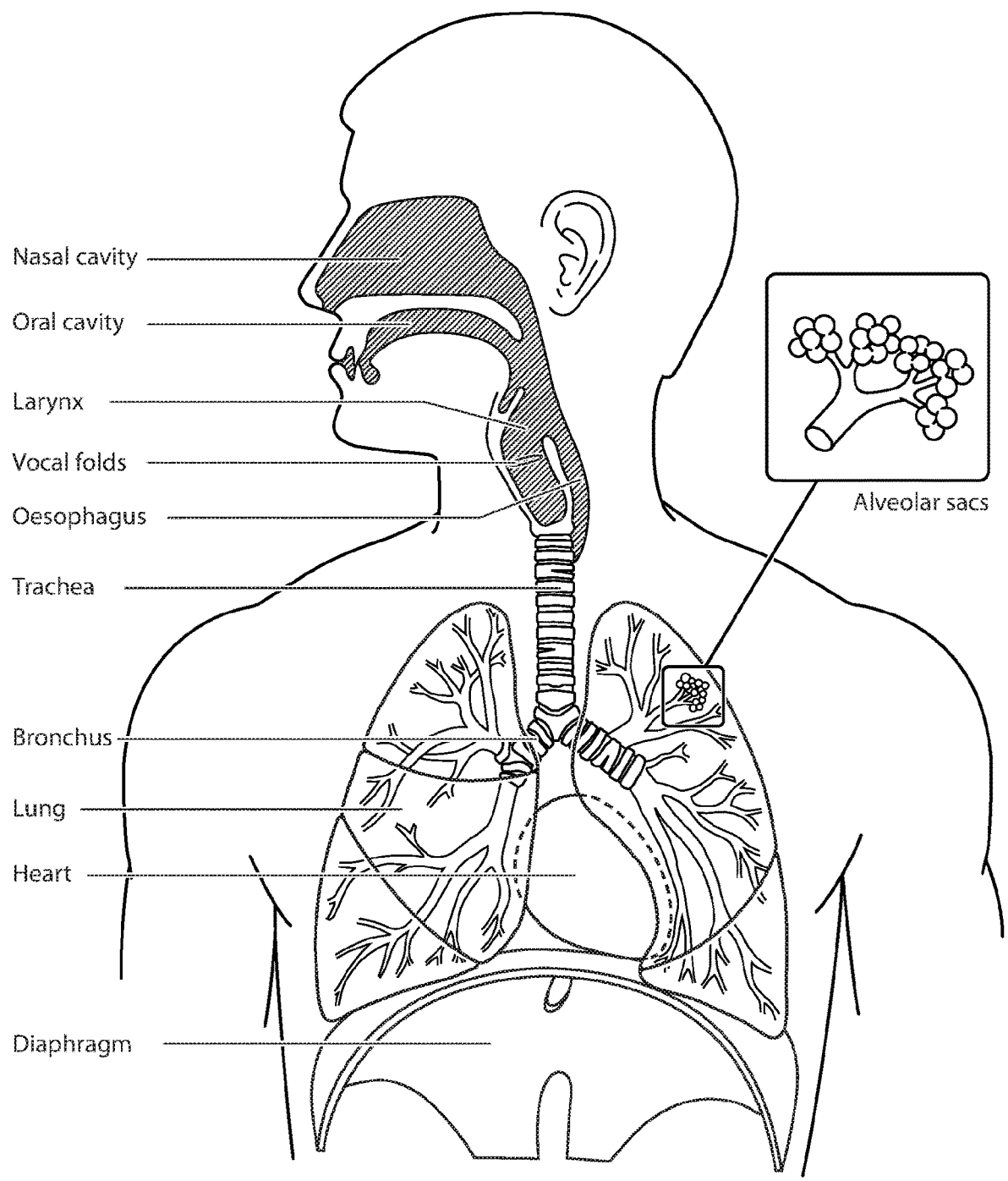
Figure 3:
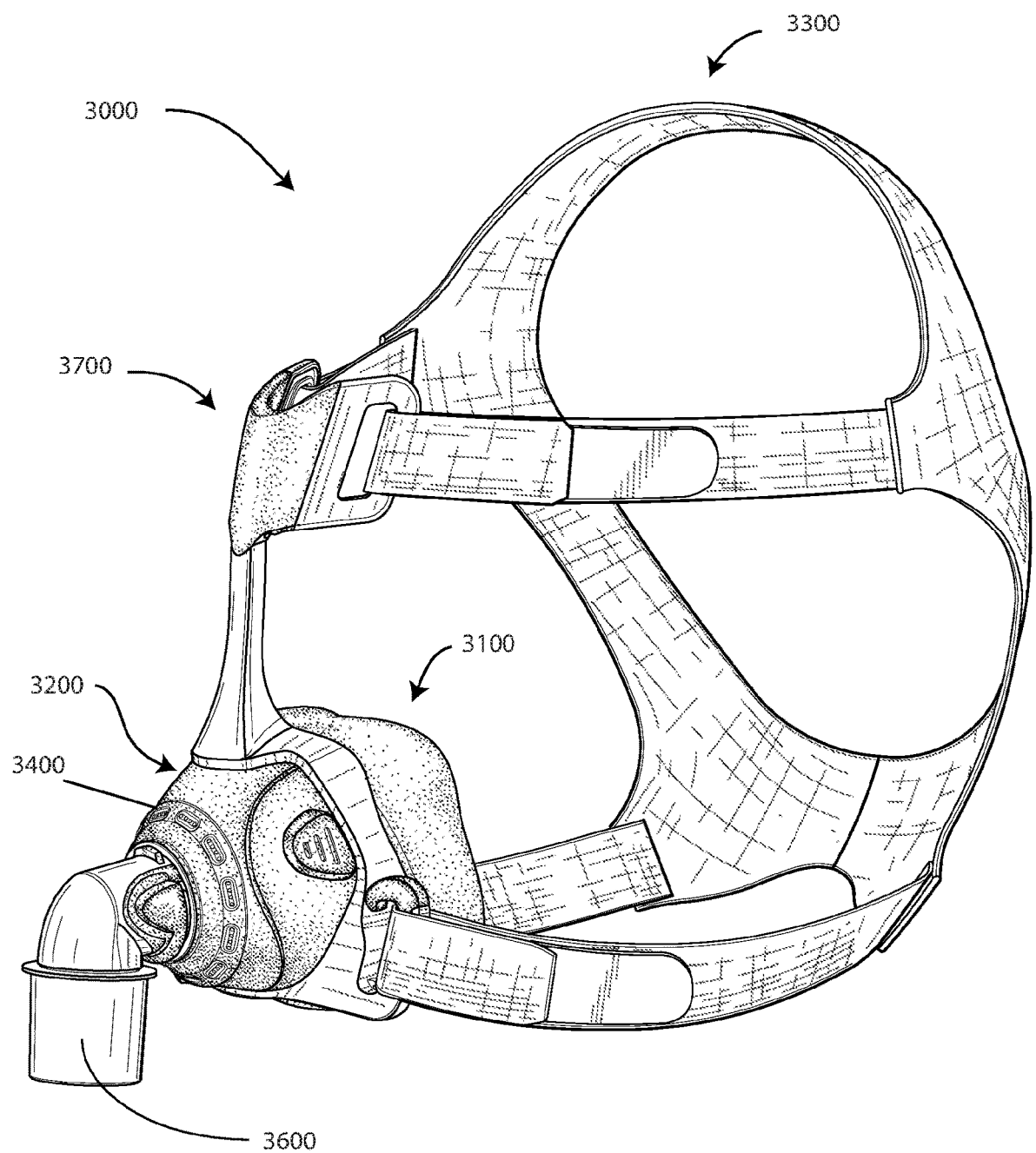
Figure 4A:
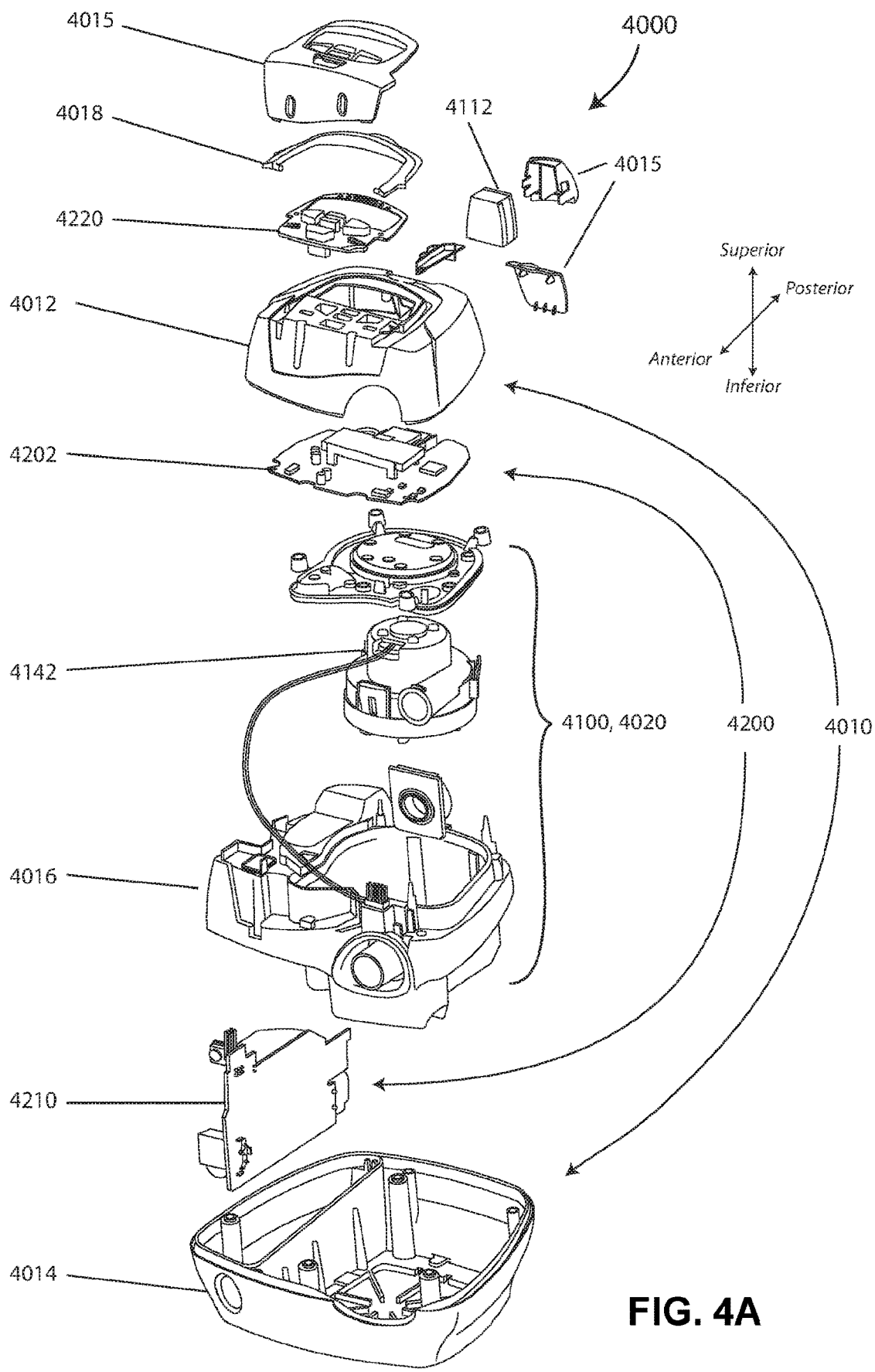
FIG. 4A shows a RPT device in accordance with one form of the present technology.
Figure 4B:
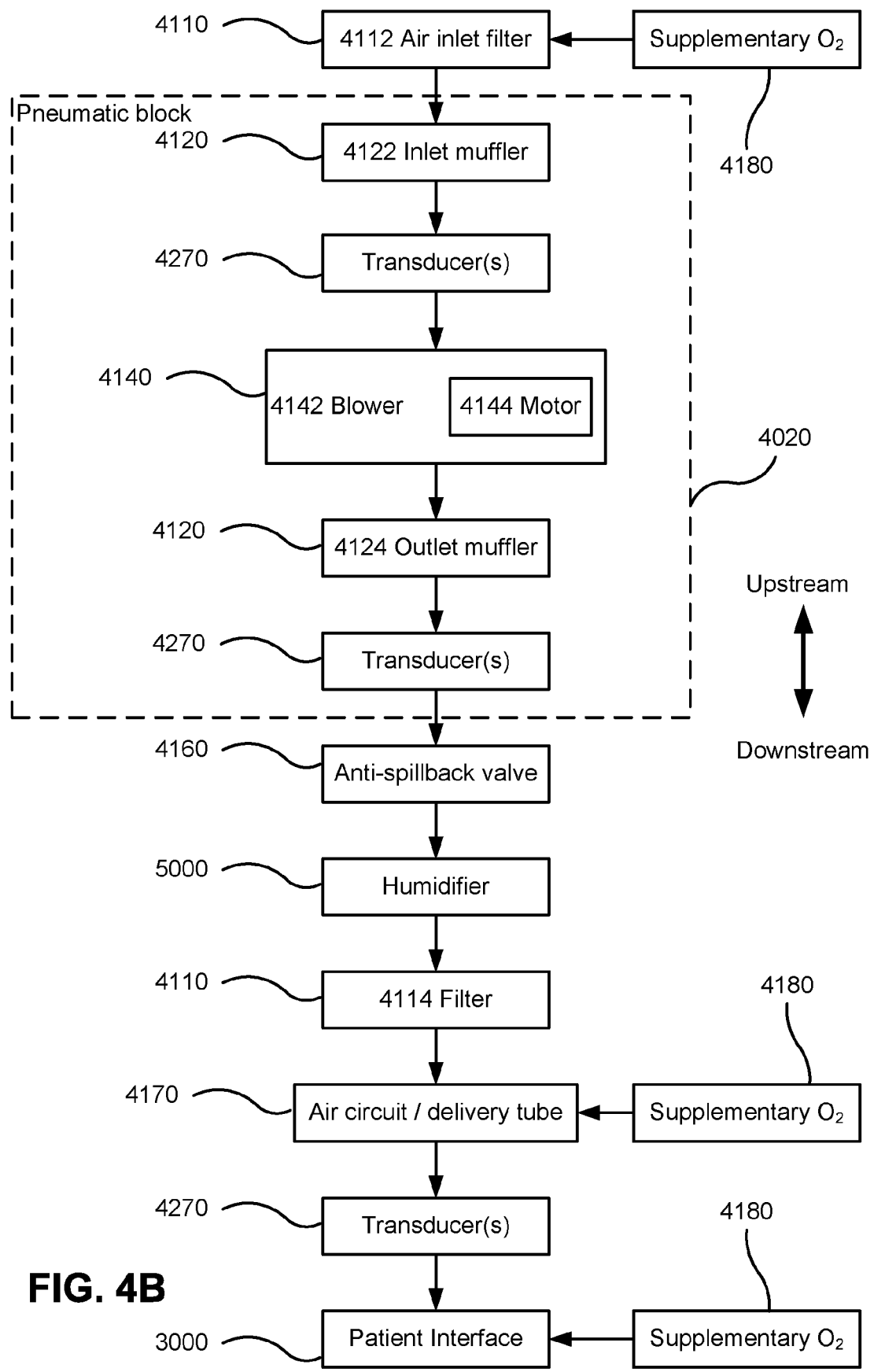
FIG. 4B is a schematic diagram of the pneumatic path of a RPT device in accordance with one form of the present technology. The directions of upstream and downstream are indicated.
Figure 4C:
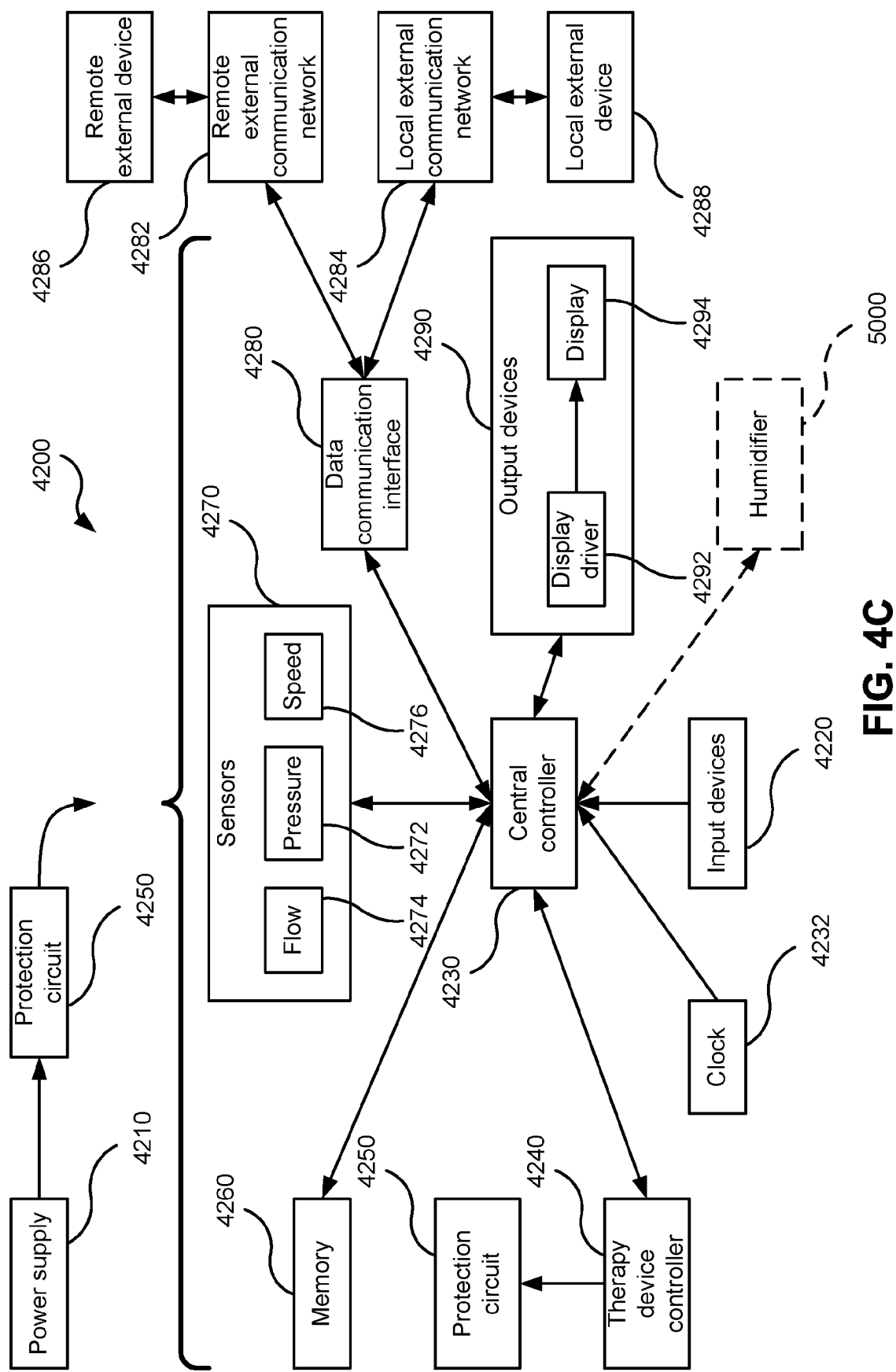
FIG. 4C is a schematic diagram of the electrical components of a RPT device in accordance with one form of the present technology.
Figure 4D:
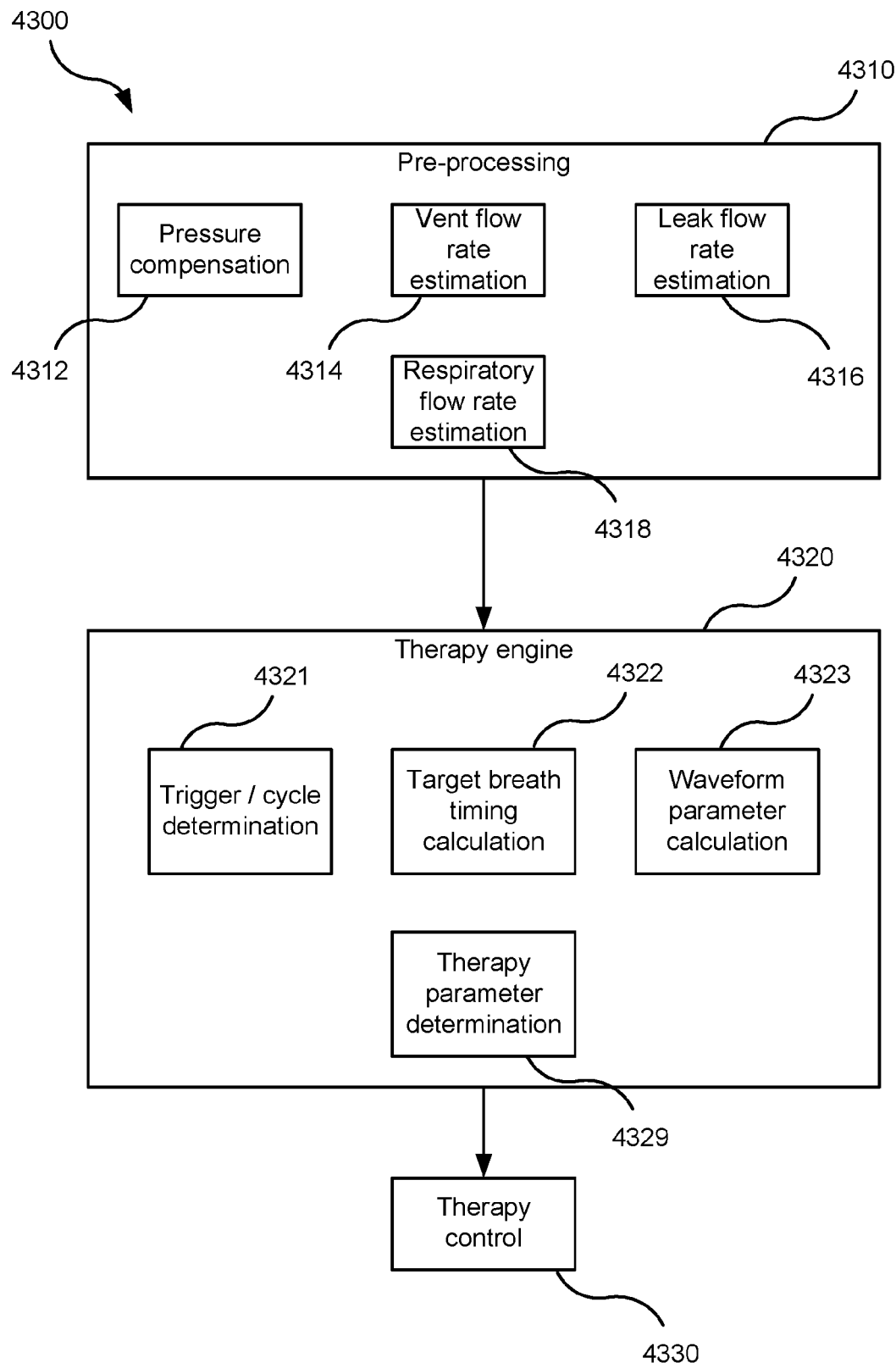
FIG. 4D is a schematic diagram of the algorithms implemented in a RPT device in accordance with one form of the present technology. In this figure, arrows with solid lines indicate an actual flow of information, for example via an electronic signal.
Figure 5:
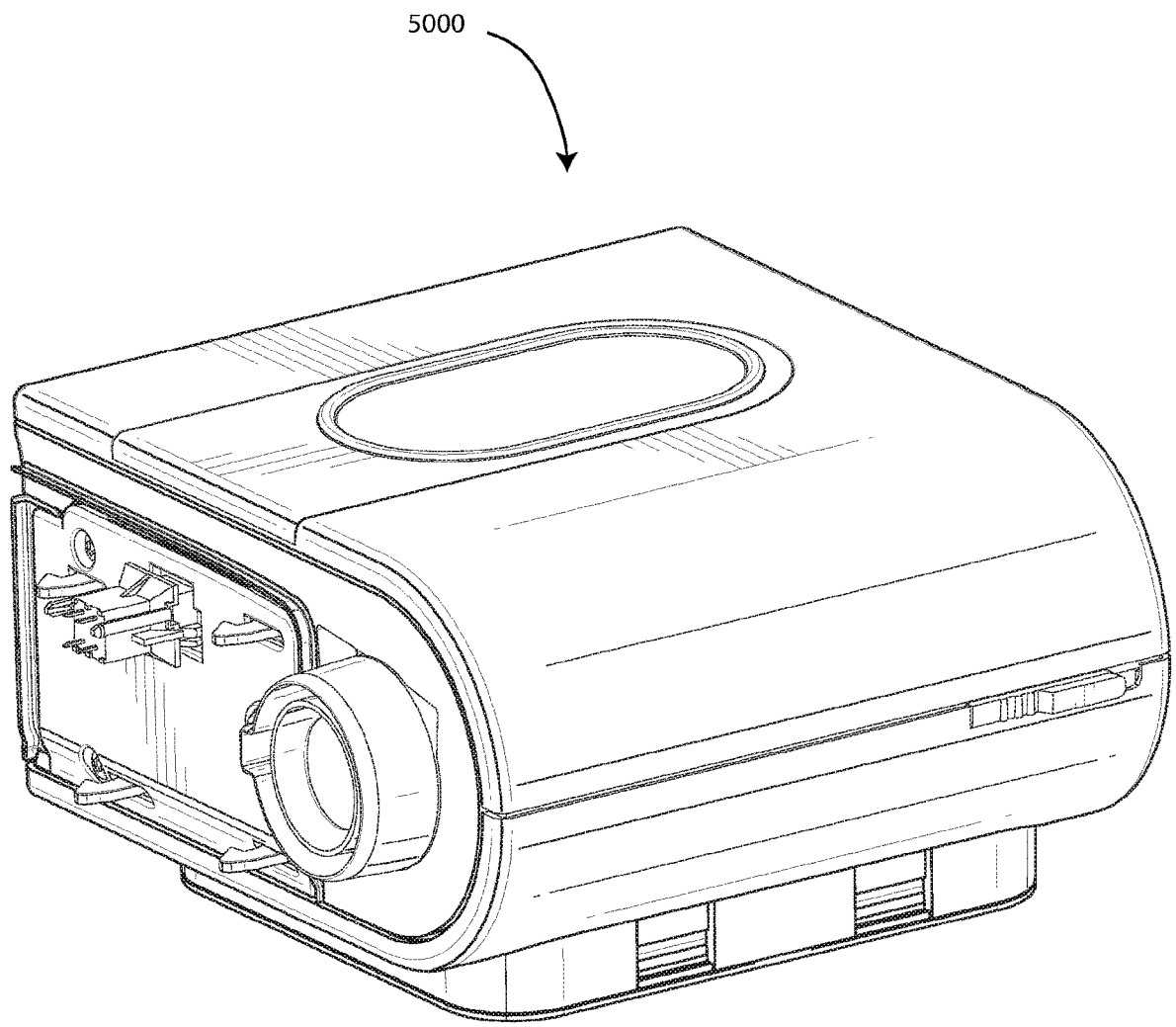

FIG. 5 shows an isometric view of a humidifier in accordance with one form of the present technology.

4.6 Breathing Waveform

Figure 6:
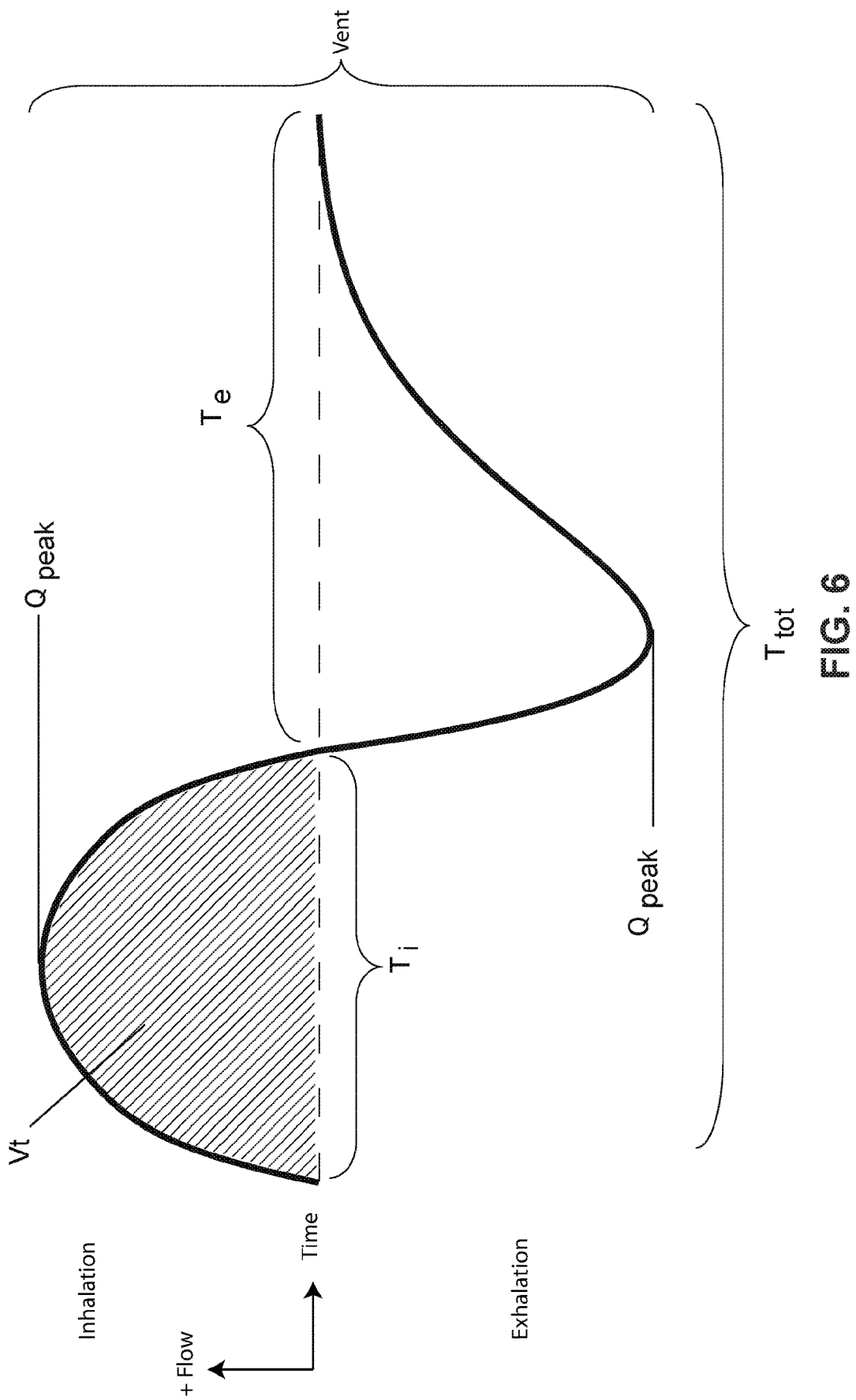

FIG. 6 shows a model typical breath waveform of a person while sleeping. The horizontal axis is time, and the vertical axis is respiratory flow rate. While the parameter values may vary, a typical breath may have the following approximate values: tidal volume Vt, 0.5 L, inspiratory time Ti, 1.6 s, peak inspiratory flow rate Qpeak, 0.4 L/s, expiratory time Te, 2.4 s, peak expiratory flow rate Qpeak, −0.5 L/s. The total duration of the breath (respiratory time), Ttot, is about 4 seconds. An adult typically breathes at a rate of about 15 breaths per minute (BPM), with Ventilation, Vent, about 7.5 L/minute. A typical duty cycle, the ratio of Ti to Ttot, is about 40%.

4.7 Pressure Waveforms

Figure 7:
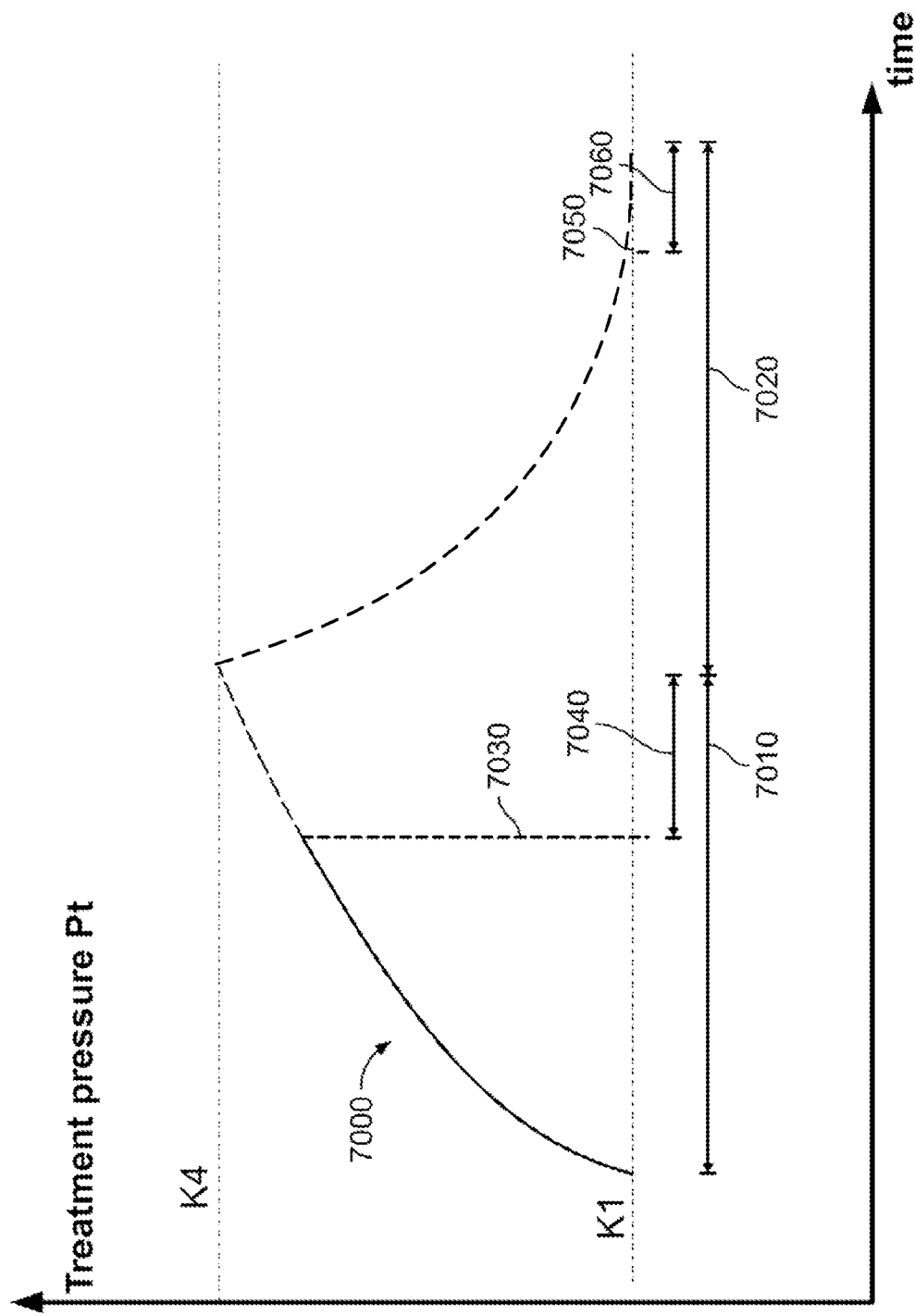

FIG. 7 illustrates an example treatment pressure waveform in accordance with one form of the present technology.

4.8 Treatment Methods

Figure 8:
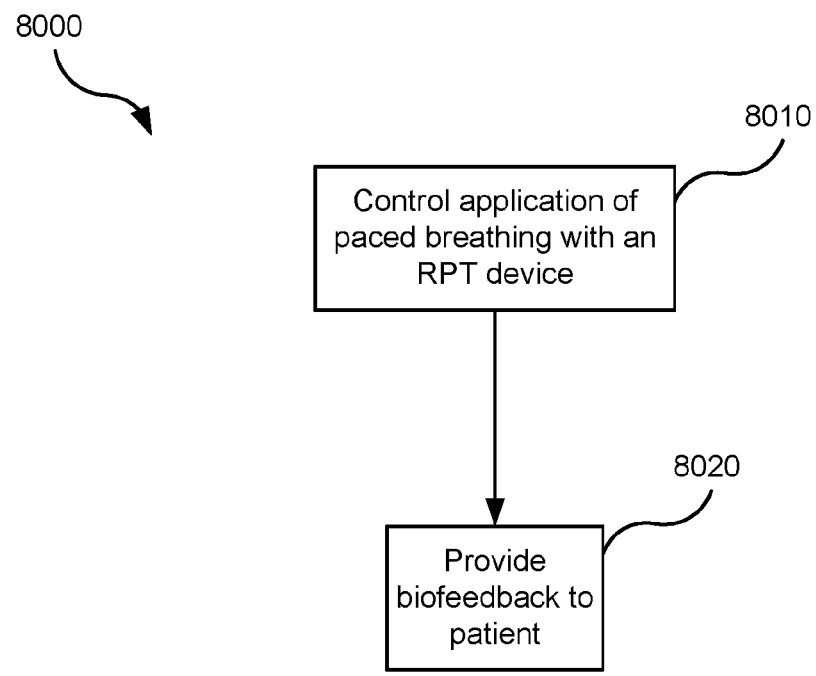

FIG. 8 illustrates an example method of insomnia therapy according to one form of the present technology.

Figure 9:
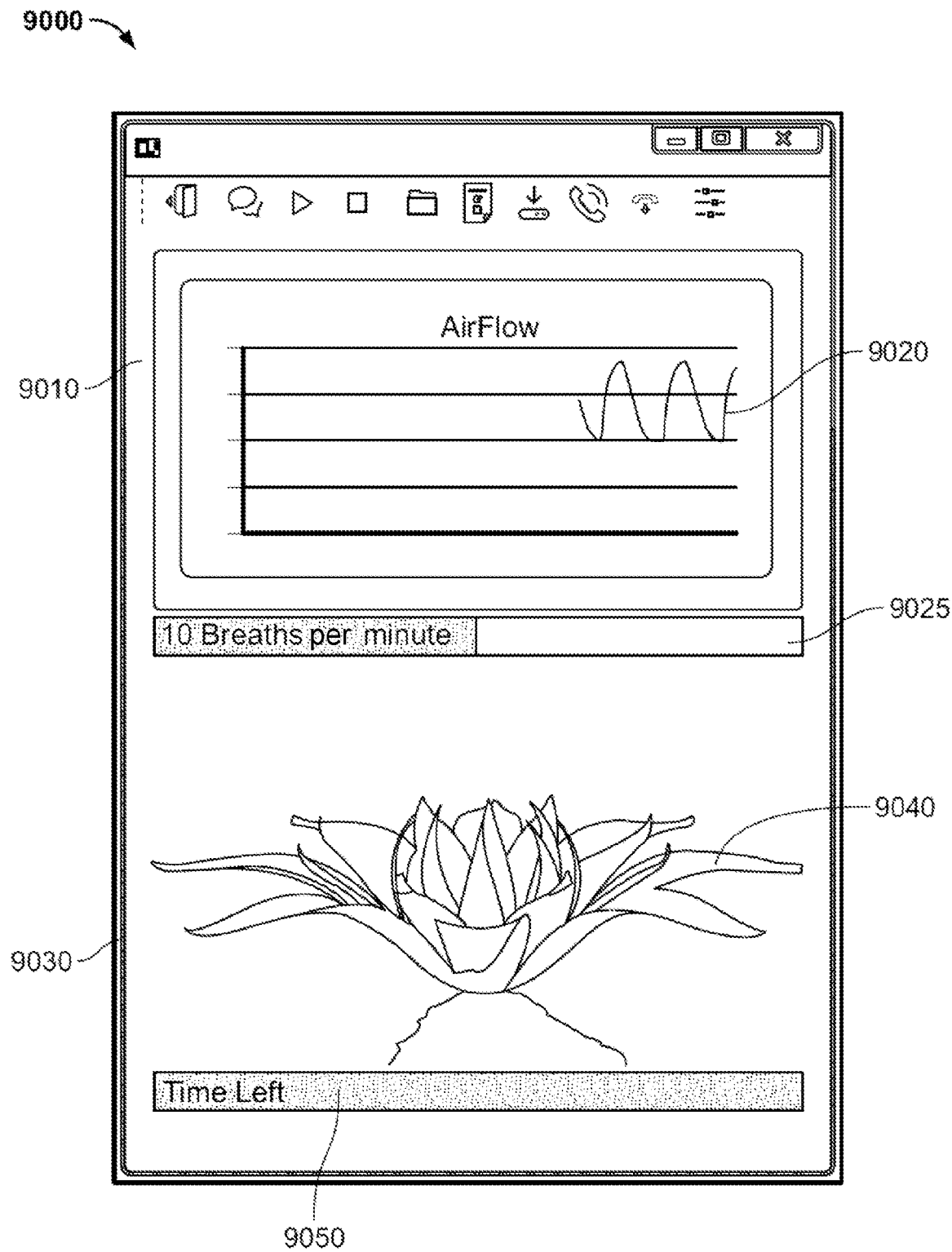

FIG. 9 shows one example of a screenshot generated by a software application (an "app") as part of the biofeedback step of the method of FIG. 8.

Figure 10:
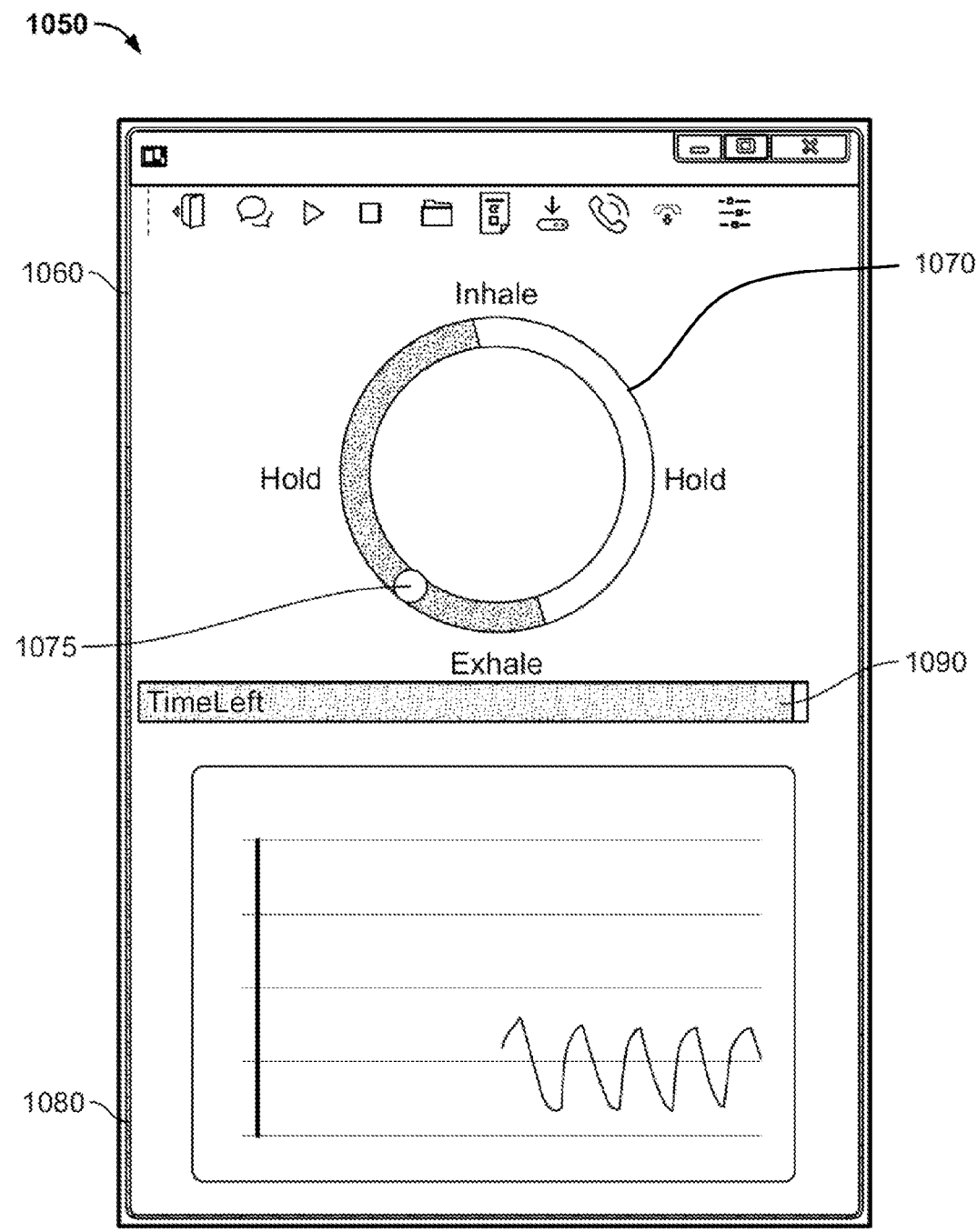

FIG. 10 shows another example of a screenshot generated by an "app" as part of the biofeedback step of the method of FIG. 8.

Figure 11:
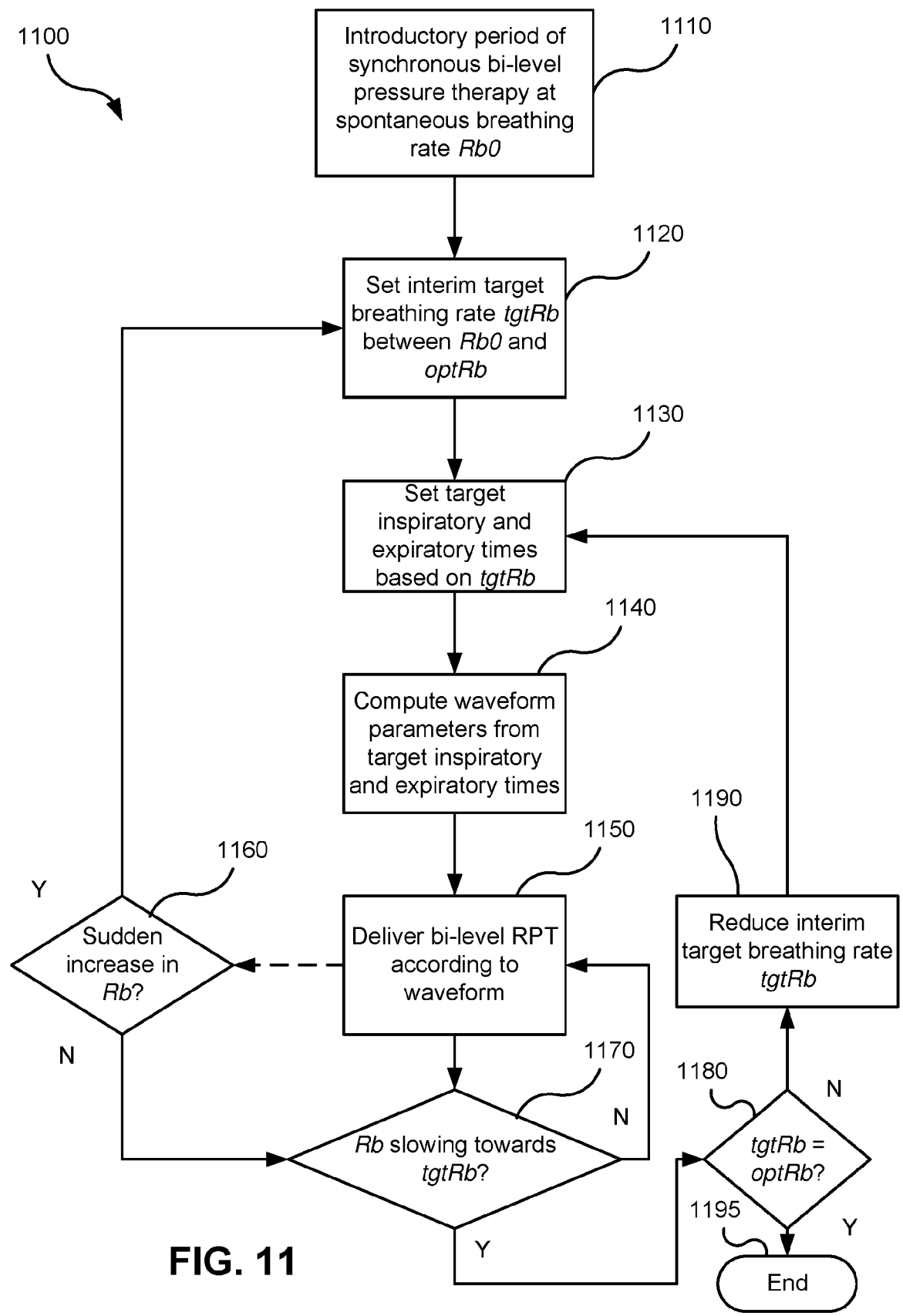

FIG. 11 is a flow chart illustrating a method of implementing the paced breathing step of the method of FIG. 8.

5. DETAILED DESCRIPTION OF EXAMPLES OF THE

Technology

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating insomnia, comprising the step of applying positive pressure to the entrance of the airways of a patient 1000.

5.2 Treatment Systems

In one form, the present technology comprises an apparatus or device for treating insomnia. The apparatus or device may comprise a RPT device 4000 for supplying pressurised air to the patient 1000 via an air circuit 4170 to a patient interface 3000.

5.3 Patient Interface

A non-invasive patient interface 3000 in accordance with one form of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

An unsealed patient interface, in the form of a nasal cannula, includes nasal prongs which can deliver air to respective nares of the patient 1000. Such nasal prongs do not generally form a seal with the inner or outer skin surface of the nares. The air to the nasal prongs may be delivered by one or more air supply lumens that are coupled with the nasal cannula. The lumens lead from the nasal cannula via the air circuit 4170 to an RPT device that generates the flow of air, possibly at high flow rates. The "vent" at the unsealed patient interface, through which excess airflow escapes to ambient, is the passage between the end of the prongs of the cannula via the patient's nares to atmosphere.

5.4 RPT Device

An RPT device 4000 in accordance with one form of the present technology comprises mechanical and pneumatic components 4100, electrical components 4200 and is configured to execute one or more algorithms 4300. The RPT device has an external housing 4010, possibly formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g. an inlet air filter 4112, an inlet muffler 4122, a pressure generator 4140 capable of supplying air at positive pressure (e.g. a blower 4142), an outlet muffler 4124 and one or more transducers 4270, such as pressure sensors 4272 and flow sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

A RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g. the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate such as a total flow rate Qt from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit

An air circuit 4170 in accordance with one form of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inspiration and expiration. In other cases a single limb is used.

5.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components

5.4.2.1 Power Supply

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.3 Central Controller

In one form of the present technology, the central controller 4230 is one or a plurality of processors suitable to control a RPT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280, and humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with a RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, preferably non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which are stored computer program instructions expressing the one or more methodologies described herein, such as the one or more algorithms 4300.

5.4.2.8 Data Communication Systems

In one preferred form of the present technology, a data communication interface 4280 is provided, and is connected to the central controller 4230. Data communication interface 4280 may be connectable to remote external communication network 4282 and/or a local external communication network 4284. Remote external communication network 4282 may be connectable to remote external device 4286. Local external communication network 4284 may be connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, "smartphone", tablet computer, "smart watch", smart television, or remote control, etc.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

In an alternative implementation, the RPT device may be a mask-mounted RPT device such as the RPT device disclosed in PCT publication no. WO2018/018074, the entire contents of which are herein incorporated by reference.

5.4.3 RPT Device Algorithms

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.3.1.1 Pressure Compensation

In one form of the present technology, a pressure compensation algorithm 4312 receives as an input a signal indicative of the pressure Pd in the pneumatic path proximal to an outlet of the pneumatic block, and a signal indicative of the flow rate Qd of air being supplied from an outlet of the pneumatic block. The pressure compensation algorithm 4312 estimates the pressure drop through the air circuit 4170 using the device flow rate Qd and provides as an output an estimated pressure, Pm, in the patient interface 3000, as the outlet pressure Pd minus the estimated pressure drop.

5.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate, Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a time-varying treatment pressure Pt.

In various forms, the therapy engine module 4320 comprises one or more of the following sub-modules that have algorithms such as: trigger/cycle determination 4321, target breath timing determination 4322, waveform parameter determination 4323, and therapy parameter determination 4329.

5.4.3.2.1 Trigger/Cycle Determination

According to some forms of the present technology, a trigger/cycle determination algorithm 4321 may be a module that receives as an input a signal indicative of respiratory flow Qr. The module may provide as an output a binary variable indicating the current state of the breathing cycle of the patient, either inspiration (0) or expiration (1).

The breathing state variable may then "toggle" from 1 to 0 and from 0 to 1 upon detecting the start of spontaneous inspiration and expiration respectively. The spontaneous "trigger points" and "cycle points" are the instants at which the breathing state variable changes from 1 to 0 and from 0 to 1, respectively. In one implementation of trigger/cycle determination, the breathing state variable is determined to toggle to 0 (thereby "triggering" the RPT device 4000) when the respiratory flow rate Qr exceeds an inspiratory threshold, and toggles to 1 (thereby "cycling" the RPT device 4000) when the respiratory flow rate Qr falls below an expiratory threshold. In one implementation, the expiratory threshold is calculated as a predetermined fraction, e.g. 10%, of a recent average peak (inspiratory) flow rate Qpeak, while the inspiratory threshold is set to zero.

The inspiratory time Ti and the expiratory time Te of a given breath may be respectively obtained by subtracting the trigger point from the cycle point, and the cycle point from the trigger point of the following breath. The total (respiratory) time Ttot is the sum of the inspiratory time Ti and the expiratory time Te of the breath.

5.4.3.2.2 Target Breath Timing Calculation

According to the present technology, a target breath timing calculation algorithm 4322 may be a module that receives as an input a signal indicative of respiratory flow rate Qr, the inspiratory time Ti and the expiratory time Te. The module may provide as outputs a target inspiratory time tgtTi and a target expiratory time tgtTe. (The sum of the target inspiratory time tgtTi and the target expiratory time tgtTe is the target total (respiratory) time tgtTtot.) The manner in which the target breath timing calculation algorithm 4322 calculates the target inspiratory time tgtTi and the target expiratory time tgtTe is described in detail below.

5.4.3.2.3 Waveform Parameter Calculation

In some forms of the present technology, the therapy parameter determination algorithm 4329 may be a module that provides a treatment pressure Pt that varies over each respiratory cycle of the patient 1000 according to a predetermined parametrised treatment pressure waveform Pt(t).

In such forms of the present technology, a waveform parameter determination algorithm 4323 receives as input the target inspiratory time tgtTi and the target expiratory time tgtTe and, applying one or more functions to the input value(s), provides as output a set of waveform parameters for the parametrised treatment pressure waveform that cues the patient to achieve the target inspiratory time tgtTi and the target expiratory time tgtTe. Optionally, the waveform parameter determination algorithm derives the set of waveform parameters such that they can be applied to one or more functions to generate a parametrised pressure waveform as illustrated in FIG. 7 that varies according to a curve (non-linear) within an inspiration portion and a distinct curve (non-linear) within an expiration portion. In this regard, the waveform parameters are provided to the therapy parameter determination algorithm 4329.

In one such form one or more functions for generating the parametrised treatment pressure waveform are in two-part form, a target inspiratory portion (time t between 0 (the trigger point) and the target inspiratory time tgtTi) and a target expiratory portion (time t between the target inspiratory time tgtTi (the cycle point) and the target total time tgtTtot). An example two-part function for generating a parametrised treatment pressure waveform is described by the following:

$$Pt(t) = \begin{cases} K1 + (K2 \times t)^{K3}, & 0 < t \leq tgtTi \\ K4 - (K5 \times (t - tgtTi))^{K6}, & tgtTi < t \leq tgtTtot \end{cases} \quad (1)$$

where K1 to K6 are the waveform parameters. Thus, functions of (1) may be implemented by the therapy parameter determination algorithm 4329.

FIG. 7 contains an illustration of the parametrised waveform 7000 of equation (1). The waveform 7000 is designed with patient comfort in mind, refraining from sudden changes in pressure. The waveform 7000 rises smoothly from the pressure K1 (the EPAP) to the pressure K4 (the IPAP) during the target inspiratory portion 7010, and falls smoothly from the pressure K4 to the pressure K1 during the target expiratory portion 7020. In the example waveform 7000, the spontaneous cycle point 7030 occurs before the end of the target inspiratory portion 7010, but the pressure continues to rise until the target inspiratory time tgtTi is reached. The portion of the waveform 7000 between the cycle point 7030 and the end of the target inspiratory portion 7010 is the "inspiration hold" portion 7040, whose function is to cue or encourage the patient to breathe in for the full target inspiratory time tgtTi. Likewise, in the example waveform 7000, the spontaneous trigger point 7050 occurs before the end of the target expiratory portion 7020. Optionally, as shown in FIG. 7, the pressure may continue to fall to the pressure K1 after the spontaneous trigger point 7050, or alternatively continue to equal the expiratory pressure K1 (not shown), until the target expiratory time tgtTe is reached. The portion of the waveform 7000 between the trigger point 7050 and the end of the target expiratory portion 7020 is the "expiration hold" portion 7060, whose function is to cue or encourage the patient to breathe out for the full target expiratory time tgtTe.

In one form of the present technology, the EPAP K1 and the IPAP K4 are predetermined values such as 3 cmH$_2$O and 8 cmH$_2$O respectively, providing a moderate pressure swing (IPAP-EPAP difference) of 5 cmH$_2$O. The inspiratory and expiratory exponents K3 and K6 may be predetermined values, such as 0.5 and −3 respectively, providing a reasonable rate of rise and fall in pressure during inspiration and expiration respectively. The inspiratory coefficient K2 is then chosen such that the target inspiratory portion, following equation (1), reaches the IPAP pressure K4 after the target inspiratory time tgtTi. Likewise, the expiratory coefficient K5 is chosen such that the target expiratory portion, following equation (1), reaches the EPAP pressure K1 after the target expiratory time tgtTe.

In an alternative form, the inspiratory exponent K3 and the inspiratory coefficient K2 may be jointly manipulated such that the target inspiratory portion, following equation (1), reaches the IPAP pressure K4 after the target inspiratory time tgtTi. Likewise, the expiratory exponent K6 and the expiratory coefficient K5 may be jointly manipulated such that the target expiratory portion, following equation (1), reaches the EPAP pressure K1 after the target expiratory time tgtTe.

5.4.3.2.4 Therapy Parameter Determination

In some forms of the present technology, the central controller 4230 executes a therapy parameter determination algorithm 4329 that may determine one or more therapy parameters using the values returned by one or more of the other algorithms in the therapy engine module 4320.

In some forms of the present technology, the therapy parameter is an instantaneous treatment pressure Pt. In one implementation of this form, the therapy parameter determination algorithm 4329 determines the treatment pressure Pt at the current time t by inserting the waveform parameters returned by the waveform parameter calculation algorithm 4323, along with the current time t, the target inspiratory time tgtTi and the target expiratory time tgtTe, into the parametrised waveform. In one such form, the parametrised waveform is given by equation (1) and the waveform parameters are K1 to K6.

5.4.3.3 Therapy Control Module

The therapy control module 4330 in accordance with one form of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.5 Humidifier

In one form of the present technology there is provided a humidifier 5000 (e.g. as shown in FIG. 5) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

5.6 Treatment Methods

The parametrised waveform of equation (1) implements bi-level respiratory pressure therapy, in that a treatment pressure Pt determined using equation (1) oscillates between two values or levels in rough synchrony with the patient's respiratory cycle. That is, the therapy parameter determination algorithm 4329 increases the treatment pressure Pt from a base pressure K1 (the EPAP) to a maximum pressure K4 (the IPAP) during inspiration, and decreases the treatment pressure Pt from K4 back to K1 during expiration.

In one form of the present technology, insomnia therapy comprises a session of "paced breathing" of a predetermined duration. Paced breathing comprises the use of bi-level respiratory pressure therapy to slow down a patient's breathing toward an "optimal" breathing rate in a manner that is sympathetic to the response of the patient such that the therapy is well tolerated. It is established that slow-paced breathing can be calming, particularly in patients who are sympathetically over-active, such as insomniacs. The traditional yogic relaxation practice of Pranayama may be assisted by paced breathing.

A method 8000 of insomnia therapy is illustrated in FIG. 8. At step 8010, the central controller 4230 of the RPT device 4000 controls an application of paced breathing for a patient. This step 8010 may be performed by the therapy control module 4330, informed by output parameter(s) from the therapy engine 4320 as part of the algorithms 4300 described above. Step 8010 is described in further detail below. At step 8020, biofeedback is provided to the patient. This step 8020 is described in further detail below. Steps 8010 and 8020, while shown as sequential in FIG. 8, may be performed contemporaneously (e.g., simultaneously or in parallel).

FIG. 11 is a flow chart illustrating a method 1100 that implements step 8010 in one form of the present technology. The method 1100 may start at optional step 1110 with an introductory period of bi-level respiratory pressure therapy as described above, during which the patient's spontaneous inspiratory time Ti and expiratory time Te are estimated from the respiratory flow rate Qr by the trigger/cycle determination algorithm 4321 as described above. The waveform parameter calculation algorithm 4323 uses the spontaneous inspiratory time Ti and expiratory time Te (rather than target inspiratory and expiratory times) to compute the waveform parameters K1 to K6 as described above. The therapy parameter determination algorithm 4329 uses the waveform parameters K1 to K6 along with the spontaneous inspiratory time Ti and expiratory time Te to determine the treatment pressure Pt at each time t. The result is a bi-level treatment pressure waveform that is in close to exact synchrony with the patient's spontaneous respiratory cycle, in which there are no inspiration or expiration hold portions. The patient's spontaneous breathing rate Rb during this period is saved as the starting breathing rate Rb0.

After the introductory period (step 1110), the therapy parameter determination algorithm 4329 at step 1120 sets an interim target breathing rate tgtRb that is lower than the starting breathing rate Rb0 but greater than an optimal breathing rate optRb. In one implementation, the interim target breathing rate tgtRb may be set to, for example, 10 breaths per minute or other value in a suitable range such as a value at a high end of the range such as a range between 10 and 6 BPM or other suitable rates. The optimal breathing rate optRb may be set to, for example, six breaths per minute or other value such as a value at the low end of the aforementioned range or other desired breathing rate. Step 1130 then sets a target inspiratory time and a target expiratory time based on the interim target breathing rate tgtRb. The reciprocal of the interim target breathing rate tgtRb, i.e. the target total time tgtTtot, which is larger than the current total time Ttot, may be partitioned into a target inspiratory time tgtTi and a target expiratory time tgtTe. In other words, the sum of the target inspiratory time tgtTi and the target expiratory time tgtTe is the target total time tgtTtot. In one implementation of step 1130, the target inspiratory time tgtTi and the target expiratory time tgtTe are set to be in the same proportion as the spontaneous inspiratory time Ti and expiratory time Te. In other implementations of step 1130, the target inspiratory time tgtTi and the target expiratory time tgtTe may be set to be in a predetermined target proportion such as 1 to 2, 1 to 1, or 2 to 3.

Step 1140 uses the target inspiratory time tgtTi and expiratory time tgtTe to compute the waveform parameters K1 to K6 as described above.

At step 1150, bi-level respiratory pressure therapy is delivered. The therapy parameter determination algorithm 4329 uses the waveform parameters K1 to K6 along with the target inspiratory time tgtTi and target expiratory time tgtTe to determine the treatment pressure Pt at each time t. This causes the bi-level treatment pressure waveform, and in particular the inspiration hold and expiration hold portions thereof, to encourage the patient's spontaneous inspiratory time Ti and expiratory time Te to increase to the target inspiratory time tgtTi and the target expiratory time tgtTe.

The step 1170 checks whether the patient's breathing rate Rb is slowing down toward the current interim target breathing rate tgtRb. If not ("N"), therapy continues at step 1150. If so ("Y"), step 1180 checks whether the interim target breathing rate tgtRb has reached the optimal breathing rate optRb. If so ("Y"), the method 1100 concludes at step 1195. If not ("N"), step 1190 reduces the interim target breathing rate tgtRb. In one implementation, step 1190 reduces the interim target breathing rate tgtRb according to a predetermined schedule. Such a predetermined schedule may, for example, include a step reduction such as a step reduction of 1 breath per minute or other reduction (e.g., one half breath per minute reduction) between successive target breathing rates of the schedule. The method 1100 then returns to step 1130.

Step 1160, contemporaneously (e.g., simultaneously) with the delivery step 1150, checks for a sudden increase in the patient's breathing rate Rb, such as occurs during an arousal. If there is no such increase ("N"), the method 1100 continues to step 1170. If such a sudden increase occurs ("Y"), the method 1100 aborts the schedule of reduction of interim target breathing rate tgtRb and returns to step 1120 to begin the reductions again from the start of the schedule. Optionally, the aborted operation (i.e., "Y" in step 1160) may instead lead to a provision of a predetermined interval of synchronous bi-level respiratory pressure therapy at the spontaneous breathing rate, which may optionally be implemented by returning to step 1110 from step 1160 before returning to step 1120.

Parameters of the paced breathing such as the schedule of reduction of interim target breathing rate tgtRb and/or the predetermined target proportion of target inspiratory time tgtTi to target expiratory time tgtTe may vary over different paced breathing sessions. For example, as the patient becomes more accustomed to paced breathing over multiple sessions, the schedule may set out a more rapid reduction of the interim target breathing rate tgtRb. In such a case, the schedule may have different step reductions between rates and the applied step reduction of a given session may be increased relative to a step reduction of a prior session, such as (a) a function of a number of sessions with the paced breathing apparatus or (b) a function of determined time(s) for completion of the pacing process (e.g., an interval from step 1120 through to the end at step 1195) such as where the determined time decreases from a prior determined time or decreases by a predetermined amount.

The biofeedback provided at step 8020 of the method 8000 further improves the effectiveness of the paced breathing of step 8010 in slowing breathing rates. The biofeedback, which may take periodic form such as a calming animation (e.g. a flower repeatedly folding and unfolding, or a ball repeatedly rolling around a circle) and/or calming sounds (e.g. tones that repeatedly rise and fall), may, if synchronised with the pressure variations of the paced breathing step 8010, further encourage the patient's breathing to slow to the interim target breathing rate tgtRb. The biofeedback may be provided via a local external device 4288 that communicates with, and is generally under the control of, the RPT device 4000 via the local network 4284 such as with a wired or wireless communication link(s). A local external device 4288 suitable for this purpose may be a personal computer, "smartphone", tablet computer, projector, "smart watch", smart television, networked television, or "smart glasses", etc. A controller of the local external device 4288, e.g. a microprocessor, may be configured to implement the biofeedback (step 8020) by program instructions stored on a memory of the local external device 4288. The program instructions may be invoked at the start of an insomnia therapy session.

FIG. 9 shows one example of a screenshot 9000 of an animated display (such as with an animated graphic image) generated by an "app" comprising such program instructions, wherein the local external device 4288 is a smartphone with a display screen. The display screen may have multiple views, such as in an upper portion and a lower portion relating to the user's breathing. The upper portion 9010 of the screenshot 9000 may contain a trace 9020 representing the respiratory flow rate Qr of the patient 1000 during therapy. The trace 9020 is animated and continually updates as new values of respiratory flow rate Qr are received by the app from the RPT device 4000 via the local network connection 4284.

Between the upper portion 9010 and the lower portion 9030, the app may generate a bar 9025 indicating the current breathing rate Rb relative to the optimal breathing rate optRb. In one implementation, the portion of the bar 9025 that is filled with colour indicates the difference between the patient's current breathing rate Rb and the optimal breathing rate optRb, as a fraction of the difference between the patient's starting breathing rate Rb0 and the optimal breathing rate optRb. In FIG. 9 the bar 9025 is half-filled, indicating that the patient's current breathing rate Rb is about halfway between the patient's starting breathing rate Rb0 and the optimal breathing rate optRb. The bar may be repeatedly updated during therapy such as to present animated movement of the portion of the bar. Thus, as the current breathing rate changes, the presentation of the extent of the coloured portion of the bar similarly changes.

The lower portion 9030 of the screenshot 9000 contains a frame from an animation. The animation shows a representation 9040 of a flower (e.g., a lotus flower) opening and closing at the interim target breathing rate tgtRb. In one implementation, the lotus flower closes during the target inspiratory portion (of duration tgtTi) and opens during the target expiratory portion (of duration tgtTe).

The animation may be accompanied by acoustic biofeedback that is also synchronised with the interim target breathing rate tgtRb. As the flower closes, a synthesised voice instructs the patient to breathe in. As the flower opens, the voice instructs the patient to breathe out. The voice may be accompanied by an acoustic tone or combination of tones (a chord) whose pitch is higher during inspiration and lower during expiration. The voice and/or the tone may become silent (e.g., fade) after a few cycles as the animation continues.

Below the lower portion 9030, the app may generate a bar 9050 indicating the elapsed time in the therapy session relative to the predetermined duration of the therapy session. In one implementation, the portion of the bar 9050 that is filled with colour indicates the time elapsed as a fraction of the predetermined duration of the therapy session.

FIG. 10 shows another example 1050 of a screenshot of an animated display generated by an app comprising such program instructions, wherein the local external device 4288 is a smartphone with a display screen.

The lower portion 1080 of the screenshot 1050 contains a flow rate trace similar to the upper portion 9010 of the screenshot 9000 of FIG. 9. The upper portion 1060 of the screenshot 1050 contains a frame from an animated annular graphic 1070 representing the respiratory cycle of the patient 1000. The right-hand portion of the annular graphic 1070, which in one implementation is coloured blue, represents the target inspiratory portion of the respiratory cycle, and the left hand portion, which in one implementation is coloured purple, represents the target expiratory portion of the respiratory cycle. A marker graphic such as an animated ball 1075 graphic is generated to move in relation to a target graphic. For example, the ball 1075 may be presented as tracing along or circulating around the annular graphic 1070 at the interim target breathing rate tgtRb. That is, the ball 1075 moves repeatedly around the annular graphic 1070, with each complete circuit taking the target total time tgtTot. The ball 1075 traverses the right-hand (inspiratory) portion (e.g., from about 0 to 180 degrees) of the annular graphic 1070 during the target inspiratory portion and traverses the left-hand (expiratory) portion (e.g., from about 180 to 360 degrees) of the annular graphic 1070 during the target expiratory portion. In one implementation, the ball 1075 moves at a constant speed, and the target inspiratory and expiratory portions of the annular graphic 1070 have respective lengths in the same proportion as the target inspiratory time tgtTi and the target expiratory time tgtTe. For example, if tgtTi/tgtTe is equal to 4/5, the target inspiratory portion may be from 0 to 160 degrees and the target expiratory portion may be from 160 to 360 degrees. In another implementation, the target inspiratory and expiratory portions of the annular graphic 1070 have equal lengths, and the ball 1075 moves at different speeds through the target inspiratory portion and the target expiratory portion to achieve the target breath timing.

In one implementation, the marker graphic or ball 1075 is a constant colour, e.g. yellow. In another implementation, a display characteristic of the marker graphic (e.g., the ball 1075), such as colour, changes depending on how well the patient's breathing is synchronised with the target breath timing. For example, the ball 1075 is green when the patient's breathing is in synchrony with the target breath timing, and it may progress to become redder as the patient's breathing departs further from the target breath timing (or target breathing rate). Similarly, as the patient approaches the target breath timing (or target breathing rate), the colour of the ball 1075 may be change to progress from redder to green. Thus, the display characteristic of the ball may vary according to a difference, such as a timing difference, between the target breathing rate or breath timing and a spontaneous breathing rate or breath timing of the patient.

A modification of the method 1100 may be used to implement step 8020 so as to synchronise the biofeedback with the paced breathing step 8010. The modifications are that step 1140 computes parameters of the biofeedback (rather than parameters of a waveform) from the target inspiratory and expiratory times, and step 1150 generates the biofeedback according to the computed parameters rather than, or in addition to, the control of the generation of the bi-level RPT.

The device that implements step 8020, for example the local external device 4288, may be configured to do so under the control of the central controller 4230 of the RPT device 4000, which controls the invocation of the method 8000. Alternatively, the device (e.g., the local external device 4288) may enable the patient to control the invocation of the method 8000 by activation of dedicated controls on an interface of the device (e.g., the local external device 4288), such as a "start" control and a "stop" control. In one such implementation, the device (e.g., the local external device 4288) that implements step 8020 may also be configured to enable a user such as the patient or a clinician to set parameters of the paced breathing step 8010, such as the IPAP, the EPAP, the starting breathing rate Rb0, and the optimal breathing rate optRb, by activation of dedicated controls on the interface of the device (e.g., the local external device 4288).

Other forms of biofeedback may also, or alternatively, be provided under step 8020. Examples, which may be used alone or in combination, include:

Visual biofeedback such as changing colours;
Audio biofeedback such as calming music;
Haptic biofeedback such as vibration (e.g. via a "smart watch") or compression (e.g. via a compression vest or a "hugging robot").
Thermal biofeedback, e.g. via cooling headgear
Olfactory biofeedback such as gas delivery, e.g. nitrous oxide.
A "womb room" combining multiple sensory forms of biofeedback.

The disclosed insomnia therapy may also be used:
To aid acclimatisation to patient interface and RPT device before starting conventional respiratory therapy for conditions such as OSA and respiratory failure.
As a pre-sleep preparation to enhance a patient's conventional respiratory therapy for conditions such as OSA and respiratory failure.
In alternation with conventional respiratory therapy for conditions such as OSA and respiratory failure, depending on the patient's sleep state such as by detection of such states. For example, the disclosed therapy may be activated for use when the patient is awake, while the conventional respiratory therapy may be activated for use during sleep.
To reduce arousability during sleep, improving sleep quality.
To reduce sympathetic nervous system drive with positive implications for conditions frequently comorbid with insomnia, e.g. hypertension, CHF, atrial fibrillation, coronary artery disease, and diabetes.
As a regular daytime "calming" therapy for an awake patient.

In an alternative implementation of insomnia therapy, the biofeedback of step 8020 is used contemporaneously (e.g. simultaneously) with respiratory pressure therapy or high flow therapy rather than the paced breathing of step 8010. As the patient's breathing rate reaches each successive interim target breathing rate in the schedule, the parameters of the respiratory pressure therapy or flow therapy may be adjusted accordingly, to further encourage the patient's breathing rate to slow toward the optimum breathing rate. For example, the treatment pressure of the respiratory pressure therapy or the flow rate of the high flow therapy may be reduced as the patient's breathing rate reaches each successive interim target breathing rate in the schedule.

The disclosed insomnia therapy apparatus may include one or more sensors configured to generate signals representing the state of hyperarousal of the patient. Such sensors may include one or more of:

Core temperature sensor
Skin temperature sensor
Skin conductivity sensor
Photoplethysmograph (PPG) for heart rate
Respiratory inductance plethysmograph (chest band) for respiratory rate
Accelerometer for actigraphy In addition, the patient's interactions with the local external device 4288 may provide an indication of their level of hyperarousal. For example, if the interactions are fast and irregular, this may be an indication of heightened arousal.

Signals from the one or more sensors may be used to generate an estimate of hyperarousal, such as a hyperarousal index, representing the patient's current state of hyperarousal. The hyperarousal index may in turn be used to condition the disclosed insomnia therapy, such that the therapy is more aggressive when the hyperarousal index is higher.

One or more of the above hyperarousal sensors may be co-located or integrated with the device providing haptic biofeedback. In one example, the hugging robot is configured with one or more hyperarousal sensors that are configured to generate signals on contact with the patient.

5.7 GLOSSARY

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms of CPAP therapy, the pressure at the entrance to the airways will be slightly higher during expiration, and slightly lower during inspiration. In some forms, the pressure will vary between respiratory cycles of the patient, for example being increased in response to detection of indications of partial upper airway obstruction, and decreased in the absence of indications of partial upper airway obstruction.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Bi-level respiratory pressure therapy: Respiratory pressure therapy in which the treatment pressure oscillates between two values or levels in rough synchrony with the patient's respiratory cycle. Typically, the treatment pressure increases to a maximum level during inspiration, and decreases to a minimum level during inspiration.

Insomnia: Problems falling and staying asleep, or non-restorative sleep that persist(s) longer than one month and result in functional impairment. Two kinds of insomnia are observed:

(i) sleep onset insomnia: difficulty falling asleep;
(ii) sleep maintenance insomnia: frequent awakenings during the night or early morning awakenings.

Hyperarousal: A state of increased psychological and physiological tension marked by such effects as reduced pain tolerance, anxiety, exaggeration of startle responses, insomnia, fatigue and accentuation of personality traits.

Post-Traumatic Stress Disorder (PTSD): The development of characteristic symptoms following exposure to an extreme traumatic stressor event. The characteristic symptoms include persistent re-experiencing of the traumatic event (flashbacks), persistent avoidance of stimuli associated with the trauma, and persistent symptoms of increased arousal. All symptoms must persist for more than one month and cause clinically significant distress or impaired function. Post-traumatic stress disorder is common, frequently does not remit without intervention, and results in high levels of functional impairment and health care costs. Violent crimes, including rape and physical assaults, combat exposure, and natural disasters constitute examples of traumatic events that can involve threat to integrity of the self or others and can be accompanied by intense fear, helplessness, or horror. Community prevalence estimates of PTSD range from 1% to 10%, with higher estimates reported in victims of interpersonal violence (20% to 30%) and combat veterans (15%-30%).

Adherent: Continuing with treatment.
Compliant: Continuing with treatment for an extended duration.

5.7.2 Respiratory Cycle

Apnea: According to some definitions, an apnea is said to have occurred when flow falls below a predetermined threshold for a duration, e.g. 10 seconds. An obstructive apnea is said to have occurred when, despite patient effort, some obstruction of the airway does not allow air to flow. A central apnea is said to have occurred when an apnea is detected that is due to a reduction in breathing effort, or the absence of breathing effort, despite the airway being patent. A mixed apnea is said to have occurred when a reduction or absence of breathing effort coincides with an obstructed airway.

(Spontaneous) breathing rate (Rb): The rate of spontaneous respiration of a patient, usually represented in breaths per minute, and computable as 60 divided by the total time Ttot.

Duty cycle: The ratio of inspiratory time, Ti to total time, Ttot.

Effort (breathing): The work done by a spontaneously breathing person attempting to breathe.

Expiratory portion of a breathing cycle: The period from the start of expiratory flow to the start of inspiratory flow.

Flow limitation: The state of affairs in a patient's respiration where an increase in effort by the patient does not give rise to a corresponding increase in flow rate. Where flow limitation occurs during an inspiratory portion of a breathing cycle it may be described as inspiratory flow limitation. Where flow limitation occurs during an expiratory portion of a breathing cycle it may be described as expiratory flow limitation.

Hypopnea: According to some definitions, a hypopnea is said to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort. In one form in adults, either of the following may be regarded as being hypopneas:
 (i) a 30% reduction in patient breathing for at least 10 seconds plus an associated 4% desaturation; or
 (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow during the inspiratory portion of the respiratory flow waveform.

Respiratory disturbance index (RDI): Apnea-Hypopnea Index plus RERA index.

Respiratory Event Related Arousal (RERA): A sequence of breaths lasting at least 10 seconds characterized by increasing respiratory effort or by flattening of the inspiratory portion of the flow rate waveform leading to arousal from sleep, when the sequence of breaths does not meet criteria for an apnea or hypopnea.

Respiratory flow rate, patient airflow rate, respiratory airflow rate (Qr): These synonymous terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inspired or expired during normal breathing, when extra effort is not applied.

Inspiratory (inspiration) Time (Ti): The duration of the inspiratory portion of the respiratory flow rate waveform.

Expiratory (expiration) Time (Te): The duration of the expiratory portion of the respiratory flow rate waveform.

Respiratory (total) Time (Ttot): The total duration between the start of one inspiratory portion of a respiratory flow rate waveform and the start of the following inspiratory portion of the respiratory flow rate waveform.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both inspiratory and expiratory flow, per unit time. When expressed as a volume per minute, this quantity is often referred to as "minute ventilation". Minute ventilation is sometimes given simply as a volume, understood to be the volume per minute.

5.7.3 RPT Device Parameters

Flow rate (or flow): The volume (or mass) of air delivered per unit time. Flow rate may refer to an instantaneous quantity. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow rate, Qt, is the flow rate of air leaving the RPT device. Vent flow rate, Qv, is the flow rate of air leaving a vent to allow washout of expired gases. Leak flow rate, Ql, is the flow rate of leak from a patient interface system or elsewhere. Respiratory flow rate, Qr, is the flow rate of air that is received into the patient's respiratory system.

Leak: An unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g\text{-}f/cm^2$, hectopascal. 1 $cmH_2O$ is equal to 1 $g\text{-}f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

5.7.4 Terms for Ventilators

Adaptive Servo-Ventilator (ASV): A servo-ventilator that has a changeable, rather than fixed target ventilation. The changeable target ventilation may be calculated from some characteristic of the patient, for example, a respiratory characteristic of the patient.

Backup rate: A parameter of a ventilator that establishes the minimum breathing rate (typically in number of breaths per minute) that the ventilator will deliver to the patient, if not otherwise triggered by spontaneous respiratory effort.

Cycled: The termination of a ventilator's inspiratory portion. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End Expiratory Pressure (EEP): Desired mask pressure which the ventilator will attempt to achieve at the end of the expiratory portion of the breath.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

5.8 OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

5.9 REFERENCE SIGNS LIST

| | |
|---|---|
| patient | 1000 |
| screenshot | 1050 |
| upper portion | 1060 |
| annular graphic | 1070 |
| ball | 1075 |
| portion | 1080 |
| patient interface | 3000 |
| seal-forming structure | 3100 |
| plenum chamber | 3200 |
| structure | 3300 |
| vent | 3400 |
| connection port | 3600 |
| forehead support | 3700 |
| RPT device | 4000 |
| external housing | 4010 |
| upper portion | 4012 |
| portion | 4014 |
| panels | 4015 |

-continued

| | |
|---|---|
| chassis | 4016 |
| handle | 4018 |
| pneumatic block | 4020 |
| pneumatic components | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| controllable blower | 4142 |
| brushless DC motor | 4144 |
| anti-spill back valve | 4160 |
| air circuit | 4170 |
| supplemental oxygen | 4180 |
| electrical components | 4200 |
| Printed Circuit Board Assembly | 4202 |
| power supply | 4210 |
| input devices | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow sensors | 4274 |
| motor speed transducer | 4276 |
| data communication interface | 4280 |
| remote external communication network | 4282 |
| local network connection | 4284 |
| such remote external device | 4286 |
| local external device | 4288 |
| output device | 4290 |
| display driver | 4292 |
| display | 4294 |
| algorithms | 4300 |
| pre-processing module | 4310 |
| pressure compensation algorithm | 4312 |
| vent flow rate estimation algorithm | 4314 |
| leak flow rate estimation | 4316 |
| respiratory flow rate estimation algorithm | 4318 |
| therapy engine module | 4320 |
| trigger/cycle determination algorithm | 4321 |
| target breath timing calculation algorithm | 4322 |
| waveform parameter calculation algorithm | 4323 |
| therapy parameter determination algorithm | 4329 |
| therapy control module | 4330 |
| humidifier | 5000 |
| illustration | 7000 |
| target inspiratory portion | 7010 |
| target expiratory portion | 7020 |
| cycle point | 7030 |
| trigger point | 7050 |
| method | 8000 |
| step | 8010 |
| step | 8020 |
| screenshot | 9000 |
| upper portion | 9010 |
| trace | 9020 |
| bar | 9025 |
| portion | 9030 |
| representation | 9040 |
| bar | 9050 |
| method | 1100 |
| step | 1110 |
| step | 1120 |
| step | 1130 |
| step | 1140 |
| step | 1150 |
| step | 1160 |
| step | 1170 |
| step | 1180 |
| step | 1190 |
| step | 1195 |

The invention claimed is:

1. A method of determining settings for control of bi-level respiratory pressure therapy for slowing a patient's breathing, the method comprising:
   determining an interim target breathing rate that is less than a current spontaneous breathing rate of the patient;
   deriving a target inspiratory time and a target expiratory time, each of the target inspiratory time and the target expiratory time being derived based on the interim target breathing rate;
   computing, with one or more first functions, a set of parameters for generating a variable treatment pressure waveform based on the target inspiratory time and the target expiratory time, wherein the set of parameters comprise a plurality of pressure values and a plurality of exponents, wherein the plurality of pressure values represent endpoints of the variable treatment pressure waveform during inspiratory and expiratory phases of the variable treatment pressure waveform, and the plurality of exponents shape a curvature of the variable treatment pressure waveform during the inspiratory and expiratory phases;
   determining pressure settings by generating the variable treatment pressure waveform with the computed set of parameters and one or more second functions; and
   reducing the interim target breathing rate in response to a subsequent spontaneous breathing rate of the patient slowing down toward the interim target breathing rate; and
   controlling a blower to generate the bi-level respiratory pressure therapy according to the determined pressure settings.

2. The method of claim 1, wherein the one or more second functions when applied with the computed set of parameters generate the variable treatment pressure waveform with an inspiratory portion having a continuous rise until the target inspiratory time is reached.

3. The method of claim 1, wherein the one or more second functions when applied with the computed set of parameters generate the variable treatment pressure waveform with an expiratory portion having a continuous fall until the target expiratory time is reached.

4. The method of claim 1, wherein the one or more second functions are in two-part form, wherein one part generates a target inspiratory portion between a trigger point and the target inspiratory time, and wherein the other part generates a target expiratory portion between a cycle point and a target total time.

5. The method of claim 4, wherein the one or more second functions for the target inspiratory portion have a parametrised form as follows:

$$K1 + (K2 \times t)^{K3}$$

wherein t represents time and K1, K2, and K3 are parameters of the computed set of parameters or more second functions for the target inspiratory portion.

6. The method of claim 5, wherein the one or more second functions for the target expiratory portion have a parametrised form as follows:

$$K4 + (K5 \times (t - \text{tgtTi}))^{K6}$$

wherein t represents time and K4, K5, and K6 are parameters of the computed set of parameters for the target expiratory portion and tgtTi is the target inspiratory time.

7. The method of claim 6, wherein computing the set of parameters comprises computing K2 such that the target inspiratory portion starts from K1 and reaches K4 when t is equal to the target inspiratory time, wherein K1 and K4 are pressure levels of the plurality of pressure values and K3 is an exponent of the plurality of exponents.

8. The method of claim 6, wherein computing the set of parameters comprises computing K5 such that the target expiratory portion starts from K4 and reaches K1 when t is equal to the target total time, wherein K1 and K4 are predetermined pressure levels and K6 is a predetermined e.

9. The method of claim 1, wherein deriving the target inspiratory time and the target expiratory time comprises:
determining a target total time as a reciprocal of the interim target breathing rate; and
partitioning the target total time into the target inspiratory time and the target expiratory time.

10. The method of claim 9, wherein the target total time is partitioned according to a predetermined target proportion.

11. The method of claim 1 further comprising recomputing, with the one or more first functions, the set of parameters for generating the variable treatment pressure waveform based on a second target inspiratory time and a second target expiratory time that are both derived with the reduced interim target breathing rate.

12. The method of claim 1, wherein reducing the interim target breathing rate comprises reducing the interim target breathing rate according to a predetermined schedule to an optimal breathing rate.

13. The method of claim 12, further comprising aborting the predetermined schedule in response to a sudden increase in the patient's breathing rate.

14. The method of claim 12 further comprising accessing a second, predetermined schedule to alter a progress of reductions of the interim target breathing rate for a new therapy session.

15. The method of claim 14 wherein the accessing of the second predetermined schedule is based on an assessment of progress of the patient's breathing rate reductions in one or more prior therapy sessions.

16. The method of claim 1, further comprising generating biofeedback for the patient, the biofeedback being configured to further encourage the patient's breathing rate to slow down toward the interim target breathing rate.

17. The method of claim 16, wherein generating biofeedback comprises:
displaying, on a graphical display, an annular graphic, wherein one portion of the annular graphic represents an inspiratory portion, and another portion of the annular graphic represents an expiratory portion, and
displaying, on the graphical display, a marker graphic moving along the annular graphic at the target breathing rate,
wherein the marker graphic traverses the inspiratory portion of the annular graphic during the target inspiratory time.

18. The method of claim 17 further comprising varying a display characteristic of the marker graphic according to a difference between the target breathing rate and a spontaneous breathing rate of the patient.

19. The method of claim 1 further comprising:
recomputing another set of the set of parameters for generating the variable treatment pressure waveform based on another target inspiratory time and another target expiratory time that are both derived with the reduced interim target breathing rate;
determining other pressure settings by generating the variable treatment pressure waveform with the computed other set of parameters and the one or more functions; and controlling the blower to generate the bi-level respiratory pressure therapy according to the determined other pressure settings.

20. A computing device comprising a display and a controller configured to execute the method of claim 1.

21. A computer-readable medium having encoded thereon computer-readable instructions that when executed by a controller of a device cause the controller to perform the method of claim 1.

22. The method of claim 1, wherein during an introductory period, the set of parameters for generating a variable treatment pressure waveform are computed based on a spontaneous patient inspiratory time and a spontaneous patient expiratory time.

23. The method of claim 1, wherein the plurality of exponents comprises an expiratory exponent and an inspiratory exponent.

24. A respiratory pressure therapy device comprising:
a blower configured to generate a variable pressure at a patient interface according to a variable treatment pressure waveform,
at least one sensor configured to detect a spontaneous breathing rate of the patient, and
a controller coupled with the blower and the at least one sensor, the controller configured to:
determine an interim breathing rate target that is less than a current spontaneous breathing rate of the patient,
derive a target inspiratory time and a target expiratory time, each of the target inspiratory time and the target expiratory time being derived based on the interim breathing rate target,
compute, with one or more first functions, a set of parameters for generating the variable treatment pressure waveform based on the target inspiratory time and the target expiratory time, wherein the set of parameters comprise a plurality of pressure values and a plurality of exponents, wherein the plurality of pressure values represent endpoints of the variable treatment pressure waveform during inspiratory and expiratory phases of the variable treatment pressure waveform, and the plurality of exponents shape a curvature of the variable treatment pressure waveform during the inspiratory and expiratory phases,
determine pressure settings for generating the variable pressure to the patient interface by generating the variable treatment pressure waveform with the computed set of parameters and one or more second functions,
reduce the interim breathing rate target in response to a subsequent spontaneous breathing rate of the patient slowing down toward the interim breathing rate target; and
control the blower according to the pressure settings.

25. The respiratory pressure therapy device of claim 24, wherein the controller is further configured to generate biofeedback for the patient.

26. The respiratory pressure therapy device of claim 25, wherein the controller is further configured to generate biofeedback for the patient by controlling a local external computing device in communication with the controller of the respiratory pressure therapy device.

* * * * *